US007807172B2

(12) United States Patent
Hoofnagle et al.

(10) Patent No.: US 7,807,172 B2
(45) Date of Patent: Oct. 5, 2010

(54) METHODS AND COMPOSITIONS FOR DETECTING THYROGLOBULIN IN A BIOLOGICAL SAMPLE

(75) Inventors: Andrew N. Hoofnagle, Seattle, WA (US); Mark Wener, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 12/139,382

(22) Filed: Jun. 13, 2008

(65) Prior Publication Data
US 2009/0042213 A1 Feb. 12, 2009

Related U.S. Application Data

(60) Provisional application No. 60/943,758, filed on Jun. 13, 2007.

(51) Int. Cl.
*A61K 39/00* (2006.01)
*C07K 7/06* (2006.01)
*C07K 7/08* (2006.01)

(52) U.S. Cl. .................... 424/185.1; 424/193.1; 514/2; 530/327; 530/328

(58) Field of Classification Search ........................ None
See application file for complete search history.

(56) References Cited

U.S. PATENT DOCUMENTS

2004/0072251 A1 4/2004 Anderson

OTHER PUBLICATIONS

Saboori et al (Clinical Exp Immunology, 1994, 98:454-458).*
Anderson, N.L., et al., "Mass Spectrometric Quantitation of Peptides and Proteins Using Stable Isotope Standards and Capture by Anti-Peptide Antibodies (SISCAPA)," Journal of Proteome Research 3(2):235-244, 2004.
Barr, J.R., et al., "Isotope Dilution-Mass Spectrometric Quantification of Specific Proteins: Model Application With Apolipoprotein A-I," Clinical Chemistry 42(10):1676-1682, 1996.
Bondar, O.P., et al., "LC-MS/MS Quantification of Zn-α2 Glycoprotein: A Potential Serum Biomarker for Prostate Cancer," Clinical Chemistry 53(4):673-678, Apr. 2007.
Consiglio, E., et al., "Characterization of Phosphate Residues on Thyroglobulin," Journal of Biological Chemistry 262(21):10304-10314, Jul. 1987.
Demers, L.M., and C.A. Spencer (eds.), "Thyroglobulin (Tg)," Laboratory Medicine Practice Guidelines, vol. 13, Laboratory Support for the Diagnosis of Thyroid Disease, National Academy of Clinical Biochemistry, Washington, D.C., 2002, pp. 55-65.
Ericsson, U.-B., et al., "A High Prevalence of Thyroglobulin Autoantibodies in Adults With and Without Thyroid Disease as Measured With a Sensitive Solid-Phase Immunosorbent Radioassay," Clinical Immunology and Immunopathology 37(2):154-162, Nov. 1985.
Feldt-Rasmussen, "Human Thyroglobulin Reference Material (CRM 457). 2nd Part: Physicochemical Characterization and Certification," Annales de Biologie Clinique 54(10-11):343-348, 1996.
Gentile, F., et al., "Identification of Hormonogenic Tyrosines in Fragment 1218-1591 of Bovine Thyroglobulin by Mass Spectrometry," Journal of Biological Chemistry 272(1):639-646, Jan. 1997.
Hoofnagle, A., and M.H. Wener, "Serum Thyroglobulin: A Model of Immunoassay Imperfection," Clinical Laboratory International 12(8):12-14, Dec. 2006.
Kloos, R.T., and E.L. Mazzaferri, "A Single Recombinant Human Thyrotropin-Stimulated Serum Thryoglobulin Measurement Predicts Differentiated Thyroid Carcinoma Metastases Three to Five Years Later," Journal of Endocrinology & Metabolism 90(9):5047-5057, Sep. 2005.
Kuhn, E., et al., "Quantification of C-Reactive Protein in the Serum of Patients With Rheumatoid Arthritis Using Multiple Reaction Monitoring Mass Spectrometry and 13C-Labeled Peptide Standards," Proteomics 4:1175-1186, 2004.
Okosieme, O.E., et al., "Thyroglobulin Antibodies in Serum of Patients With Differentiated Thyroid Cancer: Relationship Between Epitope Specificities and Thyroglobulin Recovery," Clinical Chemistry 51(4):1-6, Feb. 2005.
Pacini, F., "Follow-Up of Differentiated Thyroid Cancer," European Journal of Nuclear Medicine 29(Suppl. 2):S492-S496, Aug. 2002.
Preissner, C.M., et al., "Phantoms in the Assay Tube: Heterophile Antibody Interferences in Serum Thyroglobulin Assays," Journal of Endocrinology & Metabolism 88(7):3069-3074, Jul. 2003.
Rifai, N., et al., "Protein Biomarker Discovery and Validation: The Long and Uncertain Path to Clinical Utility," Nature Biotechnology 24(8):971-983, Aug. 2006.
Saghari, M., et al., "Efficacy of Radioiodine Therapy in the Treatment of Elevated Serum Thyroglobulin in Patients With Differentiated Thyroid Carcinoma and Negative Whole-Body Iodine Scan," Nuclear Medicine Communications 27 (7):567-572, Jul. 2006.
Sapin, R., "Insulin Immunoassays: Fast Approaching 50 Years of Existence and Still Calling for Standardization," Clinical Chemistry 53(5):810-812, 2007.
Selby, C., "Interference in Immunoassay," Annals of Clinical Biochemistry 36(Pt 6):704-721, Nov. 1999.

(Continued)

*Primary Examiner*—Laura B Goddard
(74) *Attorney, Agent, or Firm*—Christensen O'Connor Johnson Kindness PLLC

(57) ABSTRACT

The invention provides a method and reagents for determining the presence and/or amount of human thyroglobulin in a biological sample. In one embodiment, the method comprises (a) digesting a biological sample containing proteins to provide peptide fragments; (b) contacting the digested sample with a binding reagent comprising a plurality of antibodies that are capable of binding to at least one thyroglobulin peptide fragment; and (c) determining the presence and/or amount of the thyroglobulin peptide fragments that are bound to the binding reagent. In some embodiments, the binding reagent comprises a plurality of antibodies capable of binding to at least one thyroglobulin peptide fragment set forth in TABLE 1. In some embodiments, the binding regent comprises a plurality of antibodies capable of binding to at least one thyroglobulin peptide selected from the group consisting of SEQ ID NO:2, SEQ ID NO:3, and SEQ ID NO:5.

11 Claims, 10 Drawing Sheets

OTHER PUBLICATIONS

Slev, P.R., "Performance Characteristics of Seven Automated CA 15-3 Assays," American Journal of Clinical Pathology 125(5):752-757, 2006.

Spencer, C.A., "Challenges of Serum Thyroglobulin (Tg) Measurement in the Presence of Tg Autoantibodies," Journal of Endocrinology & Metabolism 89(8):3702-3704, Aug. 2004.

Spencer, C.A., "Recoveries Cannot Be Used to Authenticate Thyroglobulin (Tg) Measurements When Sera Contain Tg Autoantibodies," Clinical Chemistry 42(5):661-663, May 1996.

Spencer, C.A., et al., "Serum Thyroglobulin Autoantibodies: Prevalence, Influence on Serum Thyroglobulin Measurement, and Prognostic Significance in Patients With Differentiated Thyroid Carcinoma," Journal of Clinical Endocrinology and Metabolism 83(4):1121-1127, Apr. 1998.

Vali, M., et al., "Thyroglobulin as Autoantigen: Structure-Function Relationships," Reviews in Endocrine & Metabolic Disorders 1(1-2):69-77, Jan. 2000.

Whitley, R.J., and K.B. Ain, "Thyroglobulin: A Specific Serum Marker for the Management of Thyroid Carcinoma," Clinics in Laboratory Medicine 24(1):29-47, Mar. 2004.

Yang, S.-X., et al., "Glycosylation in Human Thyroglobulin: Location of the N-Linked Oligosaccharide Units and Comparison With Bovine Thyroglobulin," Archives of Biochemistry and Biophysics 327(1):61-70, Mar. 1, 1996.

Zöphel, K., et al., "A Highly Sensitive Thyroglobulin Assay Has Superior Diagnostic Sensitivity for Recurrence of Differentiated Thyroid Cancer in Patients Undergoing TSH Suppression," Journal of Nuclear Medicine 47(3):552-553, Mar. 2006.

* cited by examiner

Human Thyroglobulin Protein Sequence (SEQ ID NO:1)

MALVLEIFTLLASICWVSANIFEYQVDAQPLRPCELQRETAFLKQADYVPQCAEDGSFQT
VQCQNDGRSCWCVGANGSEVLGSRQPGRPVACLSFCQLQKQQILLSGYINSTDTSYLPQC
QDSGDYAPVQCDVQQVQCWCVDAEGMEVYGTRQLGRPKRCPRSCEIRNRRLLHGVGDKSP
PQCSAEGEFMPVQCKFVNTTDMMIFDLVHSYNRFPDAFVTFSSFQRRFPEVSGYCHCADS
QGRELAETGLELLLDEIYDTIFAGLDLPSTFTETTLYRILQRRFLAVQSVISGRFRCPTK
CEVERFTATSFGHPYVPSCRRNGDYQAVQCQTEGPCWCVDAQGKEMHGTRQQGEPPSCAE
GQSCASERQQALSRLYFGTSGYFSQHDLFSSPEKRWASPRVARFATSCPPTIKELFVDSG
LLRPMVEGQSQQFSVSENLLKEAIRAIFPSRGLARLALQFTTNPKRLQQNLFGGKFLVNV
GQFNLSGALGTRGTFNFSQFFQQLGLASFLNGGRQEDLAKPLSVGLDSNSSTGTPEAAKK
DGTMNKPTVGSFGFEINLQENQNALKFLASLLELPEFLLFLQHAISVPEDVARDLGDVME
TVLSSQTCEQTPERLFVPSCTTEGSYEDVQCFSGECWCVNSWGKELPGSRVRGGQPRCPT
DCEKQRARMQSLMGSQPAGSTLFVPACTSEGHFLPVQCFNSECYCVDAEGQAIPGTRSAI
GKPKKCPTPCQLQSEQAFLRTVQALLSNSSMLPTLSDTYIPQCSTDGQWRQVQCNGPPEQ
VFELYQRWEAQNKGQDLTPAKLLVKIMSYREAASGNFSLFIQSLYEAGQQDVFPVLSQYP
SLQDVPLAALEGKRPQPRENILLEPYLFWQILNGQLSQYPGSYSDFSTPLAHFDLRNCWC
VDEAGQELEGMRSEPSKLPTCPGSCEEAKLRVLQFIRETEEIVSASNSSRFPLGESFLVA
KGIRLRNEDLGLPPLFPPREAFAEQFLRGSDYAIRLAAQSTLSFYQRRRFSPDDSAGASA
LLRSGPYMPQCDAFGSWEPVQCHAGTGHCWCVDEKGGFIPGSLTARSLQIPQCPTTCEKS
RTSGLLSSWKQARSQENPSPKDLFVPACLETGEYARLQASGAGTWCVDPASGEELRPGSS
SSAQCPSLCNVLKSGVLSRRVSPGYVPACRAEDGGFSPVQCDQAQGSCWCVMDSGEEVPG
TRVTGGQPACESPRCPLPFNASEVVGGTILCETISGPTGSAMQQCQLLCRQGSWSVFPPG
PLICSLESGRWESQLPQPRACQRPQLWQTIQTQGHFQLQLPPGKMCSADYADLLQTFQVF
ILDELTARGFCQIQVKTFGTLVSIPVCNNSSVQVGCLTRERLGVNVTWKSRLEDIPVASL
PDLHDIERALVGKDLLGRFTDLIQSGSFQLHLDSKTFPAETIRFLQGDHFGTSPRTWFGC
SEGFYQVLTSEASQDGLGCVKCPEGSYSQDEECIPCPVGFYQEQAGSLACVPCPVGRTTI
SAGAFSQTHCVTDCQRNEAGLQCDQNGQYRASQKDRGSGKAFCVDGEGRRLPWWETEAPL
EDSQCLMMQKFEKVPESKVIFDANAPVAVRSKVPDSEFPVMQCLTDCTEDEACSFFTVST
TEPEISCDFYAWTSDNVACMTSDQKRDALGNSKATSFGSLRCQVKVRSHGQDSPAVYLKK
GQGSTTTLQKRFEPTGFQNMLSGLYNPIVFSASGANLTDAHLFCLLACDRDLCCDGFVLT
QVQGGAIICGLLSSPSVLLCNVKDWMDPSEAWANATCPGVTYDQESHQVILRLGDQEFIK
SLTPLEGTQDTFTNFQQVYLWKDSDMGSRPESMGCRKDTVPRPASPTEAGLTTELFSPVD
LNQVIVNGNQSLSSQKHWLFKHLFSAQQANLWCLSRCVQEHSFCQLAEITESASLYFTCT
LYPEAQVCDDIMESNAQGCRLILPQMPKALFRKKVILEDKVKNFYTRLPFQKLMGISIRN
KVPMSEKSISNGFFECERRCDADPCCTGFGFLNVSQLKGGEVTCLTLNSLGIQMCSEENG
GAWRILDCGSPDIEVHTYPFGWYQKPIAQNNAPSFCPLVVLPSLTEKVSLDSWQSLALSS
VVVDPSIRHFDVAHVSTAATSNFSAVRDLCLSECSQHEACLITTLQTQPGAVRCMFYADT
QSCTHSLQGQNCRLLLREEATHIYRKPGISLLSYEASVPSVPISTHGRLLGRSQAIQVGT
SWKQVDQFLGVPYAAPPLAERRFQAPEPLNWTGSWDASKPRASCWQPGTRTSTSPGVSED
CLYLNVFIPQNVAPNASVLVFFHNTMDREESEGWPAIDGSFLAAVGNLIVVTASYRVGVF
GFLSSGSGEVSGNWGLLDQVAALTWVQTHIRGFGGDPRRVSLAADRGGADVASIHLLTAR
ATNSQLFRRAVLMGGSALSPAAVISHERAQQQAIALAKEVSCPMSSSQEVVSCLRQKPAN
VLNDAQTKLLAVSGPFHYWGPVIDGHFLREPPARALKRSLWVEVDLLIGSSQDDGLINRA
KAVKQFEESRGRTSSKTAFYQALQNSLGGEDSDARVEAAATWYYSLEHSTDDYASFSRAL
ENATRDYFIICPIIDMASAWAKRARGNVFMYHAPENYGHGSLELLADVQFALGLPFYPAY
EGQFSLEEKSLSLKIMQYFSHFIRSGNPNYPYEFSRKVPTFATPWPDFVPRAGGENYKEF
SELLPNRQGLKKADCSFWSKYISSLKTSADGAKGGQSAESEEEELTAGSGLREDLLSLQE
PGSKTYSK

*Fig.1.*

METHODS AND COMPOSITIONS FOR DETECTING THYROGLOBULIN IN A BIOLOGICAL SAMPLE

CROSS-REFERENCE TO RELATED APPLICATION

This application claims the benefit under 35 U.S.C. §119 of U.S. Provisional Application No. 60/943,758, filed Jun. 13, 2007, which is hereby incorporated by reference.

FIELD OF THE INVENTION

This invention relates to methods and reagents for determining the presence and/or amount of human thyroglobulin in a biological sample.

BACKGROUND

This invention relates to methods and compositions for detecting thyroglobulin in a biological sample. Thyroglobulin, which is secreted from functioning thyroid tissue, is very useful as a tumor marker in the diagnosis of recurrent, residual, and metastatic thyroid cancer. The presence of thyroglobulin in the plasma/serum of patients indicates functioning thyroid tissue. Following surgery and treatment with radioactive iodine, patients with thyroid cancer should be free of all functioning thyroid tissue. Detectable thyroid tissue in these patients indicates the need for further therapy.

However, quantitation of thyroglobulin using immunoassays is problematic. Current methods of detection utilizing immunoassays, or antibody-based assays, to quantitate intact protein in patient serum samples are complicated by several limitations. Immunoassays for thyroglobulin are affected by patient autoantibodies to thyroglobulin, patient antibodies to reagent antibodies, reagent antibody saturation with analyte, and lack of standardization (Hoofnagle, A., and M. H. Wener, *Clin Lab Int* 8:12-14 (2006)). Patient autoantibodies to thyroglobulin bind to thyroglobulin epitopes, or surface features of the protein, and interfere with reagent antibodies binding to the thyroglobulin analyte in the assay, causing falsely low concentrations of thyroglobulin to be measured by traditional "sandwich" immunoassays and falsely high concentrations of thyroglobulin in radioimmunoassays. Some patients have antibodies to reagent immunoglobulins, also called human anti-mammalian antibodies, which can cause an erroneously positive result. For example, approximately 10% of patients have antibodies to thyroglobulin (Tg) that could potentially interfere with immunoassays (Kloos, R. T., et al., *J. Clin Endocrinol Metab* 90:5047-5057 (2005); Spencer, C. A., *Clin Chem* 42:661-663 (1996); Spencer, C. A., et al., *J. Clin Endocrinol Metab* 89:3702-3704 (2004)). The prevalence of Tg autoantibodies increases to 25% in patients with differentiated thyroid carcinoma (Ericsson, U. B., et al., *Clin Immonol Immunopathol* 37:154-162 (1985); Spencer, C. A., et al., *J. Clin Endocrinol Metab* 83:1121-1127 (1998); Okosieme, O. E., et al., *Clin Chem* 52:729-734 (2005)).

In certain cases, very high concentrations of thyroglobulin saturate the reagent antibodies used in immunoassays and prevent formation of tripartite reagent immunoglobulin-antigen complexes, resulting in falsely low concentrations of thyroglobulin to be measured. Lastly, because all immunoassays use different antibodies generated independently by each company, there is suboptimal standardization of thyroglobulin immunoassays, and results from one immunoassay may not be in accord with the results of another.

Therefore, a need exists for improved methods and compositions for the detection of thyroglobulin in order to more accurately detect residual, recurrent, or metastatic disease in patients afflicted with thyroid cancer.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the invention provides a method for determining the presence or amount of human thyroglobulin in a biological sample. The method comprises (a) digesting a biological sample containing proteins to provide peptide fragments; (b) contacting the digested sample with a binding reagent comprising a plurality of antibodies that are capable of binding to at least one thyroglobulin peptide fragment; and (c) determining the presence or amount of the thyroglobulin peptide fragments that bound to the binding reagent. In some embodiments, the binding reagent comprises a plurality of antibodies capable of binding to at least one thyroglobulin peptide fragment set forth in TABLE 1. In some embodiments, the binding reagent comprises a plurality of antibodies capable of binding to at least one thyroglobulin peptide selected from the group consisting of SEQ ID NO:2, SEQ ID NO:3, and SEQ ID NO:5.

In another aspect, the invention provides a composition comprising at least one thyroglobulin peptide fragment consisting of SEQ ID NO:2, SEQ ID NO:3, or SEQ ID NO:5. In some embodiments, the thyroglobulin peptide fragment is conjugated to keyhole limpet hemocyanin. In some embodiments, the composition further comprises an adjuvant for inducing an immune response in a mammalian subject.

In another aspect, the invention provides an isolated antibody which binds to a thyroglobulin peptide fragment having an amino acid sequence selected from the group consisting of SEQ ID NO:2, SEQ ID NO:3, and SEQ ID NO:5. In some embodiments, the invention provides a composition comprising a combination of a plurality of first antibodies and a plurality of second antibodies, the first and second antibodies capable of binding to a different amino acid sequence selected from the group consisting of SEQ ID NO:2, SEQ ID NO:3 and SEQ ID NO:5.

In another aspect, the invention provides a kit comprising (a) a plurality of antibodies that are capable of binding to at least one thyroglobulin peptide fragment; and (b) a reagent comprising trypsin. In some embodiments, the kit further comprises an internal standard reagent. In some embodiments, the kit comprises a plurality of antibodies that are capable of binding to at least one thyroglobulin peptide fragment set forth in TABLE 1.

In another aspect, the invention provides a method for monitoring the efficacy of treatment of a human thyroid cancer patient. The method comprises (a) digesting a biological sample containing protein obtained from the human thyroid cancer patient to provide peptide fragments; (b) contacting the digested sample with a binding reagent comprising a plurality of antibodies that are capable of binding to at least one thyroglobulin peptide fragment; and (c) determining the presence or amount of the thyroglobulin peptide fragments that bound to the binding reagent, wherein the detection of the presence of thyroglobulin peptide fragments indicates the need for further treatment. In some embodiments, the binding reagent comprises a plurality of antibodies capable of binding to at least one thyroglobulin peptide fragment set forth in TABLE 1. In some embodiments, the binding regent comprises a plurality of antibodies capable of binding to at least one thyroglobulin peptide selected from the group consisting of SEQ ID NO:2, SEQ ID NO:3 and SEQ ID NO:5.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows the protein sequence of human thyroglobulin with representative peptides underlined that are useful for practicing various embodiments of the methods of the invention, as described in Examples 1-6;

DETAILED DESCRIPTION

Figure 2:
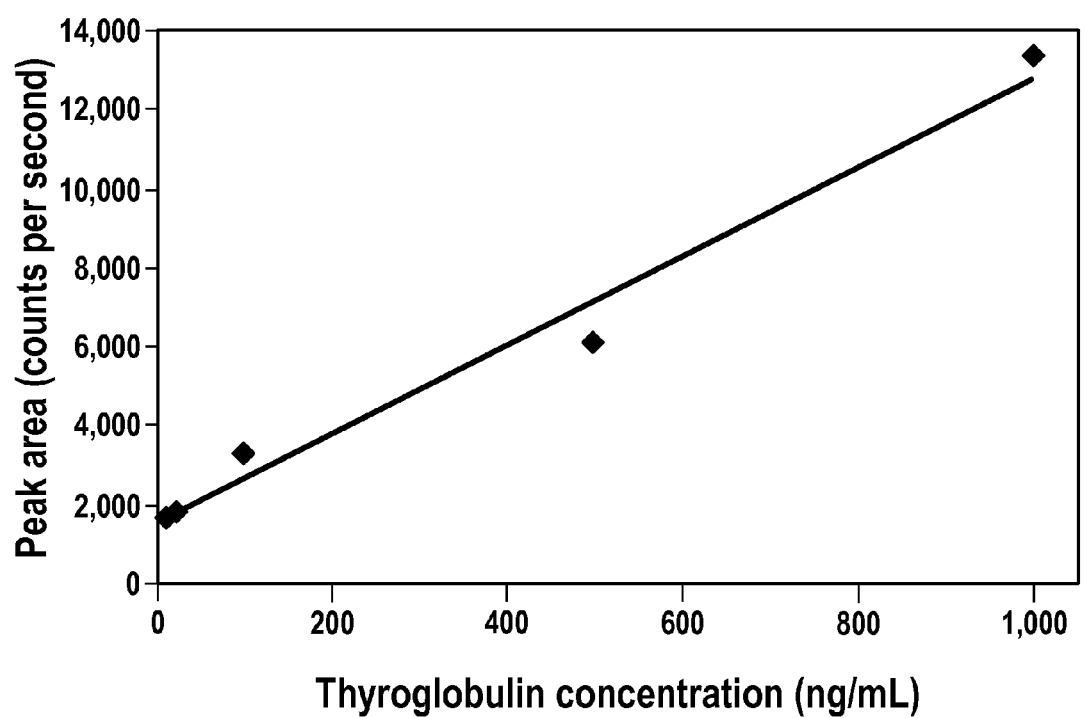
FIG. 2 graphically illustrates the quantitation of thyroglobulin in digested human serum in accordance with an embodiment of the method of the invention, as described in Example 3.

Unless specifically defined herein, all terms used herein have the same meaning as they would to one skilled in the art of the present invention.

As used herein, the term "peptide fragment" refers to any portion of a protein, such as thyroglobulin, which can be produced by a reproducible fragmentation process, such as digestion with a protease (e.g., trypsin).

As used herein, the term "antibody" refers to any of the classes of immunoglobulin molecules of any species, or any molecules derived therefrom, or any other specific binding agents constructed by variation of a conserved molecular scaffold so as to specifically bind a protein such as thyroglobulin and/or one or more peptide fragment(s) thereof. Exemplary antibodies include polyclonal, monoclonal and recombinant antibodies.

As used herein, the term "anti-peptide antibody" refers to any type of antibody (in the preceding general sense) that binds to a peptide fragment for the purposes of enrichment and/or detection of the peptide fragment from a biological sample or processed sample.

As used herein, the term "bind" or "binding" includes any physical attachment or close association, which may be permanent or temporary.

The human thyroglobulin polypeptide (SEQ ID NO:1, shown in FIG. 1) is a very large macromolecule with an apparent molecular weight of approximately 660 kDa. The predicted mass of one monomer of the homodimeric antigen is only 302 kDa. Post-translational modifications account for the remainder. These post-translational modifications include oxidation and iodination of tyrosine residues, which occurs as thyroglobulin is modified into the thyroid hormones triiodothyronine and thyroxine. Thyroglobulin exists predominantly in the colloid of the thyroid gland where it serves as a reservoir for the thyroid hormones released upon TSH stimulation of the gland. It leaks into the lymphatics surrounding functioning thyroid tissue, which subsequently circulates in the plasma. In addition, thyroglobulin is modified by phosphorylation at serine and tyrosine residues, by sulphation, and by O- and N-linked glycosylation, which may also be sulphated and phosphorylated. Importantly, around 10% of plasma thyroglobulin mass is composed of variable carbohydrate moieties. (Hoofnagle, A., and M. H. Wener, CLI 8:12-14 (2006).)

The present inventors have identified specific peptide fragments of thyroglobulin that can be detected and/or measured individually or in combination as a surrogate for the abundance or concentration of thyroglobulin in a biological sample, such as human serum. The inventors have further demonstrated that the identified specific peptides from thyroglobulin can be directly identified and quantitated as fragment ions with the correct mass that are derived from ions of correct precursor mass of an intact peptide using a suitable mass spectrometer. To help improve the sensitivity of the approach, antibodies have been generated against three of these specific peptide fragments of thyroglobulin, and these anti-peptide antibodies have been used to bind to and enrich the corresponding peptide fragments in a complex mixture of serum/plasma peptides. The use of anti-peptide antibodies to detect thyroglobulin removes the problematic interference of endogenous antibodies. In addition, because thyroglobulin peptide is directly detected using mass spectrometry rather than thyroglobulin protein being detected indirectly using antibodies, this embodiment of the method of the invention solves the problem of standardization and "hook effect" present in traditional immunoassays. Therefore, the methods and compositions provided in accordance with various embodiments of the invention may be used as a reference method for the detection of thyroglobulin in biological specimens that can be as a reference standard for comparison to results of other methods of detection of thyroglobulin and thereby improve the accuracy of detection of residual, recurrent, or metastatic disease in patients afflicted with thyroid cancer.

In accordance with the foregoing, in one aspect the invention provides a method for determining the presence or amount of human thyroglobulin in a biological sample. The method comprises (a) digesting a biological sample containing proteins to provide peptide fragments; (b) contacting the digested sample with a binding reagent comprising a plurality of antibodies that are capable of binding to at least one thyroglobulin peptide fragment; and (c) determining the presence or amount of the thyroglobulin peptide fragments that bound to the binding reagent.

The methods of the invention can be used to detect and/or measure the concentration of human thyroglobulin in any biological sample that contains protein, such as, for example, but not limited to, human blood, serum, plasma, cerebrospinal fluid, ascites, pleural effusions, pericardial effusions, and other biological fluids. In some embodiments of the method, the biological sample is human serum.

In accordance with the methods of the invention, the biological sample is digested into peptide fragments. The sample may be digested with any reagent that reproducibly generates a set of peptide fragments, such as a protease. Exemplary proteases that may be used in the methods of the invention include trypsin, endoproteinase Glu-C, endoproteinase Lys-C, endoproteinase Asp-N, pepsin, and staphylococcus protease V8.

In one embodiment of the invention, the biological sample is digested with trypsin under the appropriate conditions and for a period of time sufficient to generate peptide fragments. Any trypsin capable of reliably cleaving serum/plasma proteins would be sufficient. Trypsin preparations that may be used in the methods of the invention are commercially available, for example, from Sigma-Aldrich, Inc., or Promega, Inc. Prior to digestion, the trypsin may be optionally methylated with a methylating agent in order to render the protease resistant to self-cleavage. In accordance with various embodiments of the invention, TABLE 1 describes an incomplete set of peptide fragments (SEQ ID NOS:2-29) that are obtained from tryptic digestion of human thyroglobulin (SEQ ID NO:1).

In some embodiments, the trypsin digest is carried out in the presence of a non-ionic detergent, such as Tween 20, Tween 40, Tween 80 or Octyl-beta-D-glucopyranoside (ProClin®) at an amount from about 0.05% (w:v) to about 0.005% (w:v). In some embodiments, the trypsin digest is carried out in the presence of from about 0.05% (w:v) to about 0.005% (w:v) of Tween 20.

Once the biological sample is digested to provide peptide fragments, the digested sample is contacted with a binding reagent comprising a plurality of antibodies that are capable of binding to at least one thyroglobulin peptide fragment. In one embodiment, the sample is digested with trypsin, and the binding reagent comprises a plurality of anti-peptide fragment antibodies that bind to one or more peptide fragments set forth in TABLE 1. In another embodiment, the binding reagent comprises a plurality of antibodies capable of binding to at least one thyroglobulin peptide fragment selected from the group consisting of SEQ ID NO:2, SEQ ID NO:3, and SEQ ID NO:5. In another embodiment, the binding reagent comprises a plurality of antibodies capable of binding to at least one thyroglobulin peptide fragment selected from SEQ ID NO:2 and SEQ ID NO:3. In another embodiment, the binding reagent comprises a plurality of antibodies capable of binding to SEQ ID NO:3. In another embodiment, the binding reagent comprises a plurality of first antibodies and a plurality of second antibodies, the first and second antibodies being capable of binding to different thyroglobulin peptide fragments set forth in TABLE 1, such as, for example, SEQ ID NO:2, SEQ ID NO:3, and SEQ ID NO:5. In another embodiment, the binding reagent comprises a plurality of first antibodies, a plurality of second antibodies and a plurality of third antibodies, the first, second and third antibodies being capable of binding to different thyroglobulin peptide fragments set forth in TABLE 1, such as, for example, SEQ ID NO:2, SEQ ID NO:3, and SEQ ID NO:5. In some embodiments, the binding reagent is a solid phase reagent comprising a plurality of attached antibodies that are capable of binding to at least one thyroglobulin peptide fragment.

In accordance with the various embodiments of the methods of the invention, each anti-peptide antibody preparation may be used to directly detect or enrich a peptide fragment with an identified amino acid sequence (e.g., SEQ ID NOS: 2-29) in a digested sample containing a mixture of other peptide fragments. In one embodiment, the anti-peptide antibody preparations for use in the methods comprise antibodies that bind to SEQ ID NO:2, SEQ ID NO:3, or SEQ ID NO:5. In one embodiment, the anti-peptide preparation for use in the methods comprises antibodies that bind to SEQ ID NO:3.

The anti-peptide antibodies may be polyclonal, monoclonal, or an antibody fragment generated using any standard method. For example, a method for generating anti-peptide polyclonal antibodies is described in Example 2.

In one embodiment, the anti-peptide antibodies are monoclonal antibodies with high affinity suitable for improving the limit of detection by recovering the majority of peptides from the digestions and by permitting stringent washes to remove non-specifically bound peptides.

As used herein, the modifier "monoclonal" indicates the character of the antibody as being obtained from a substantially homogenous population of antibodies and is not to be construed as requiring production of the antibody by any particular method. Monoclonal antibodies can be obtained using any technique that provides for the production of antibody molecules by continuous cell lines in culture, such as the hybridoma method described by Kohler, G., et al., *Nature* 256:495, 1975, or they may be made by recombinant DNA methods (see, e.g., U.S. Pat. No. 4,816,567, to Cabilly). Monoclonal antibodies may also be isolated from phage antibody libraries using the techniques described in Clackson, T., et al., *Nature* 352:624-628, 1991, and Marks, J. D., et al., *J. Mol. Biol.* 222:581-597, 1991. Such antibodies can be of any immunoglobulin class including IgG, IgM, IgE, IgA, IgD and any subclass thereof.

For example, monoclonal antibodies can be obtained by injecting a suitable mammal (e.g., a BALB/c mouse) with a composition comprising a thyroglobulin polypeptide or peptide fragment thereof. After a predetermined period of time, splenocytes are removed from the mouse and suspended in a cell culture medium. The splenocytes are then fused with an immortal cell line to form a hybridoma. The formed hybridomas are grown in cell culture and screened for their ability to produce a monoclonal antibody against thyroglobulin, or the peptide fragment thereof. (See also *Current Protocols in Immunology*, Vol. 1, John Wiley & Sons, pages 2.5.1-2.6.7, 1991.)

The presence of peptide fragment bound to the anti-peptide antibody may be detected using any suitable method. Exemplary methods include mass spectrometry, capillary gel electrophoresis with mass spectrometric detection, ultraviolet absorbance detection, electrochemical detection, or flow cytometric analysis using a solid phase antibody and a second detection antibody.

In one embodiment, the peptide fragments are eluted from the binding reagent, and the enriched peptides are detected using mass spectrometry. Methods for detection of peptide fragments using mass spectrometry are known in the art and are described in U.S. Patent Publication No. 2004/0072251, to Anderson, hereby incorporated by reference. Any instrument capable of ion fragmentation and reliable quantitation may be used in accordance with the methods of the invention. For example, a triple quadrupole instrument capable of specific selection of ions with correct precursor mass in the first quadrupole, ion fragmentation in the gas phase in the second quadrupole, fragment ion selection in the third quadrupole, and ion detection by photomultiplier tube may be used to detect the enriched peptide fragments.

In some embodiments of the method, an internal standard of the peptide fragment selected for detection (as a surrogate for the parent protein) is added to the digested sample prior to detection. The internal standard may be any altered version of the respective peptide fragment that is recognized as equivalent to the peptide fragment by the appropriate binding reagent and differs from it in a manner that can be distinguished by a mass spectrometer, either through direct measurement or molecular mass, or through mass measurement of fragments (e.g., through MS/MS analysis), or by another equivalent means.

For example, the internal standard may be an isotope-labeled peptide fragment, such as described in Example 4. An isotope-labeled peptide fragment may be generated by chemical synthesis, wherein a peptide fragment identical to the natural one is made by incorporating amino acid precursors that contain heavy isotopes of hydrogen, carbon, oxygen, or nitrogen to introduce the isotopic label. In another example, a particular portion of thyroglobulin may be synthesized in an in vitro synthesis system (using recombinant techniques known to those of skill in the art) for use as an internal standard.

The internal standard is added to the digested sample at a known concentration before contacting the sample with the binding reagent. The binding reagent thus captures and enriches both the natural and the internal standard (labeled peptide) together according to their relative abundances in the sample. Since the internal standard is added at a known concentration, the ratio between the amounts of the natural and labeled forms detected by the final MS analysis allows the concentration of the natural peptide in the sample mixture to be calculated. Thus, the methods of the invention allow for the measurement of the quantity of thyroglobulin in a complex mixture, and because the selected peptide (e.g., SEQ ID NOS: 2, 3, and/or 5) is produced by complete digestion of a mixture of proteins, the abundance of the parent protein thyroglobulin (SEQ ID NO:1) in the mixture of proteins can be deduced.

In some embodiments, the method further comprises analyzing one or more external standards, or calibrators, in parallel with the methods for determining the presence or amount of thyroglobulin. The external standard, or calibrators, useful in this embodiment of the method include any solution containing a known amount of human thyroglobulin (SEQ ID NO:1), or a known amount of another polypeptide comprising SEQ ID NO:2, SEQ ID NO:3 and/or SEQ ID NO:5.

In another aspect, the invention provides a method for monitoring the efficacy of treatment of a human thyroid cancer patient. The method comprises (a) digesting a biological sample containing protein obtained from the human thyroid cancer patient to provide peptide fragments; (b) contacting the digested sample with a binding reagent comprising at least one antibody that is capable of binding to at least one thyroglobulin peptide fragment; and (c) detecting and/or measuring the amount of the thyroglobulin peptide fragments that are bound to the binding reagent, wherein the detection of thyroglobulin peptide fragments indicates the need for further treatment.

As described herein and demonstrated in Examples 1-6, the methods of the invention may be used to enrich thyroglobulin peptides from a complex mixture of serum/plasma peptides using immunoglobulins that recognize specific thyroglobulin peptides followed by direct identification and quantitation of the thyroglobulin peptides, for example, by mass spectrometry. Thyroglobulin, which is secreted from functioning thyroid tissue, is useful as a tumor marker in the diagnosis of recurrent, residual and metastatic thyroid cancer. See, e.g., Hoofnagle, et al., *CLI* 8:12-14 (2006); Whitley, R. J., et al., *Clin. Lab. Med.* 24:29-47 (2004); and Saghari, M., et al., *Nuclear Medicine Communications* 27:567-572 (2006).

The treatment for thyroid cancer typically involves the surgical removal of thyroid tissue, followed by treatment with radioactive iodine, which should eliminate all functioning thyroid tissue. Therefore, the presence of thyroglobulin in the plasma/serum of thyroid cancer patients indicates functioning thyroid tissue and the need for further therapy, such as additional surgery or radioiodine ablation. Sensitive detection of thyroglobulin permits prompt treatment of residual, recurrent, or metastatic disease. Over the past few decades, improvements in assay sensitivity have shortened the time to treatment for thyroid cancer survivors, likely leading to improved survival (Whitley, R. J., et al., *Clin Lab Med* 24:29-47 (2004)).

In another aspect, the invention provides an isolated antibody which binds to a thyroglobulin peptide fragment having an amino acid sequence selected from the group consisting of SEQ ID NO:2, SEQ ID NO:3, and SEQ ID NO:5. As described in Examples 1-3, tryptic peptide fragments set forth as SEQ ID NO:2, SEQ ID NO:3, and SEQ ID NO:5 of human thyroglobulin were identified using both liquid chromatography-electrospray ionization-tandem mass spectrometry and liquid chromatography-matrix assisted laser desorption ionization-tandem time of flight mass spectrometry. Utilization of both methods ensured that the identified peptide fragments SEQ ID NOS:2, 3, and 5 will be robust in all mass spectrometric methods currently in use. As described in Example 2, antibodies that bind the three peptides (SEQ ID NOS:2, 3, and 5) were generated and used in a detection assay for thyroglobulin, as described in Example 3.

In another aspect, the invention provides a composition comprising at least one thyroglobulin peptide fragment consisting of SEQ ID NOS:2, 3, or 5. In one embodiment, the invention provides a composition comprising at least two thyroglobulin peptide fragments consisting of SEQ ID NOS: 2, 3, or 5. In another embodiment, the invention provides a composition comprising thyroglobulin peptide fragments consisting of SEQ ID NOS:2, 3, and 5. In some embodiments, the compositions further comprise an adjuvant for inducing an immune response in a mammalian subject. In further embodiments, at least one thyroglobulin peptide in the composition is conjugated to keyhole limpet hemocyanin. The compositions comprising peptide fragments may be used to generate the anti-peptide antibodies for use in the methods of the invention.

In another aspect, the invention provides a kit comprising (a) a plurality of antibodies that are capable of binding to at least one thyroglobulin peptide fragment; and (b) a reagent comprising trypsin. In some embodiments, the kit further comprises an internal standard reagent. In some embodiments, the plurality of the antibodies in the kit are capable of binding to at least one thyroglobulin peptide fragment set forth in TABLE 1. The kit may further include one or more compositions for use in the methods described herein.

The following examples merely illustrate the best mode now contemplated for practicing the invention, but should not be construed to limit the invention.

EXAMPLE 1

This example describes the identification of the most abundant peptides liberated from human thyroglobulin during digestion of a thyroglobulin containing sample digested with trypsin, as determined using two different mass spectrometric detection techniques.

Methods:

Trypsin Digestion:

Modified trypsin (Promega, Inc.) was used. It was modified with a methylating agent in order to render the protease resistant to self-cleavage and permit more complete digestion with less enzyme.

Human thyroglobulin (Cortex, Biochem Inc., San Leandro, Calif.) was digested with modified trypsin under the following three different conditions:

Digestion 1: Tg was denatured in 3.5 mol/L urea in 100 mmol/L $NH_4HCO_3$, reduced with 5 mmol/L dithiothreitol (DTT), alkylated with 15 mmol/L iodacetamide, and then digested for 18 hours at 37° C. with modified sequencing grade trypsin (Promega, Madison, Wis.) at 100 μg Tg per mL (trypsin:Tg ratio of 1:20 w/w)

Digestion 2: Tg was digested under the same conditions as described in Digestion 1, but without reduction and alkylation;

Digestion 3: Tg was digested under the same conditions as Digestion 1, except that Tg was supplemented with normal human serum (2 μg Tg per 126 μg human serum proteins: 1.28 mg protein per mL).

The resulting thyroglobulin peptides from each trypsin digestion were purified using a hydrophilic lipophilic binding (HLB) solid phase extraction cartridge (1 mL bed volume, Waters, Milford, Mass.). After washing twice with 1 mL 0.1% formic acid in water, peptides were eluted with 80% acetonitrile, 0.3% formic acid, dried down under nitrogen, and reconstituted in 100 μl of 5% acetonitrile, 0.3% formic acid in water.

Peptides were identified using two complementary techniques:

(i) microelectrospray ionization liquid chromatography-tandem mass spectrometry (LC-MS/MS) on a Thermo-Finnigan LTQ ion trap analyzer (Waltham, Mass.). The detection of peptides was carried out using an instrument from Thermo Electron, Inc. (LTQ), which is an ion trap instrument capable of ion fragmentation in the gas phase. Ions were introduced to the mass spectrometer using a nanoflow liquid chromatography system with flow splitting to achieve stable gradients at low flow rates; and (ii) off-line HPLC-plate spotting followed by matrix assisted laser desportion ionization-tandem time of flight mass spectrometry (MALDI-TOF-TOF) with an Applied Biosystems 4700 mass analyzer (Foster City, Calif.).

For LC-TOF-TOF experiments, peptides were separated using nanoflow liquid chromatography on a system comprised of a FAMOS autosampler, Switchos column switching device, and a PROBOT MALDI plate spotting robot (Applied Biosystems, Inc.). The peptides were then identified on an ABI 4700 tandem time-of-flight instrument (Applied Biosystems, Inc.).

Results:

The results of the mass spectrometric analysis of the human thyroglobulin peptides are shown in TABLE 1.

TABLE 1

DETERMINATION OF THE BEST PEPTIDES FOR ANTIBODY PRODUCTION IN RABBITS.[A]

| | | | Peak area (Ion trap) or peak height (TOF-TOF) | | | | |
|---|---|---|---|---|---|---|---|
| | | | Linear Ion Trap | | | MALDI-TOF-TOF | |
| Peptide | SEQ ID NO: | $m/z^a$ | Digestion 1 | Digestion 2 | Digestion 3 | Digestion 1 | Hydrophobicity |
| VIFDANAPVAVR | 2 | 1272.48 | 58,210,204 | 81,447,918 | 194,201 | 51030 | −0.3 |
| LGDQEFIK | 3 | 950.07 | 55,335,595 | 53,930,998 | 34,267 | 8,802 | 0.4 |
| SHGQDSPAVYLK | 4 | 1302.42 | 47,082,888 | 123,119 | 5,659 | 5,368 | 0.0 |
| FPLGESFLVAK | 5 | 1208.43 | 44,489,374 | 65,300,983 | 111,541 | 11,170 | −0.4 |
| GGADVASIHLLTAR | 6 | 1381.56 | 42,916,756 | 41,942,023 | 118,664 | 17,907 | −0.2 |
| FLQGDHFGTSPR | 7 | 1362.48 | 40,413,027 | 64,930,010 | 55,123 | 39,950 | −0.1 |
| FLAVQSVISGR | 8 | 1177.38 | 37,065,560 | 55,773,419 | 0 | 18,100 | |
| FPDAFVTFSSFQR | 9 | 1549.71 | 33,791,534 | 42,267,723 | 75,971 | 14,392 | −0.4 |
| WESQLPQPR | 10 | 1141.26 | 30,972,286 | 56,904,484 | 0 | 20,485 | |

TABLE 1-continued

DETERMINATION OF THE BEST PEPTIDES FOR ANTIBODY PRODUCTION IN RABBITS.[A]

| Peptide | SEQ ID NO: | m/z[a] | Linear Ion Trap Digestion 1 | Linear Ion Trap Digestion 2 | Linear Ion Trap Digestion 3 | MALDI-TOF-TOF Digestion 1 | Hydro-phobicity |
|---|---|---|---|---|---|---|---|
| SQAIQVGTSWK | 11 | 1205.35 | 22,604,066 | 3,943,502 | 3,572 | 4,616 | |
| KVPTFATPWPDFVPR | 12 | 1759.04 | 22,157,262 | 13,653,736 | 55,741 | 6,121 | |
| TSGLLSSWK | 13 | 979.11 | 17,249,237 | 3,423,684 | 0 | 1,571 | |
| LALQFTTNPK | 14 | 1133.32 | 16,877,659 | 17,944,078 | 70,315 | 5,354 | |
| LRNEDLGLPPLFPPR | 15 | 1735.02 | 16,390,867 | 15,413,817 | 98,462 | 5,648 | |
| AVLM#GGSALSPAAVISHER | 16 | 1883.16 | 12,210,274 | 7,198,321 | 4,955 | 4,510 | |
| AGGENYKEFSELLPNR | 17 | 1824.97 | 10,408,136 | 9,727,929 | 0 | 15,093 | |
| AVLMGGSALSPAAVISHER | 18 | 1867.16 | 7,280,1332 | 4,535,058 | 0 | 5,511 | |
| TAFYQALQNSLGGEDSDAR | 19 | 2044.13 | 5,816,139 | 10,528,062 | 109,692 | | |
| NEAGLQC*DQNGQYR | 20 | 1653.77 | 4,599,373 | 719,823 | 0 | | |
| RAVLM#GGSALSPAAVISHER | 21 | 2039.35 | 4,308,195 | 1,608,455 | 0 | | |
| LEDIPVASLPDLHDIER | 22 | 1933.15 | 3,722,758 | 8,297,059 | 68,482 | 2,904 | |
| IMQYFSHFIR | 23 | 1342.59 | 2,551,140 | 8,873,673 | 0 | 3,920 | |
| ELFVDSGLLRPMVEGQSQQFSVSENLLK | 24 | 3152.57 | 2,069,760 | 7,314,594 | 31,510 | | |
| KPGISLLSYEASVPSVPISTHGR | 25 | 2396.73 | 1,893,836 | 5,039,748 | 19,749 | 3,170 | |
| RFSPDDSAGASALLR.S | 26 | 1563.70 | 1,798,745 | 2,111,330 | 0 | 512 | |
| R.SHGQDSPAVYLKK.G | 27 | 1430.59 | 1,515,236 | 491,341 | 0 | 675 | |
| R.LAAQSTLSFYQR | 28 | 1385.55 | 1,413,785 | 2,014,669 | 0 | 14,309 | |
| ETEEIVSASNSSR | 29 | 1409.44 | 66,054 | 0 | 0 | 675 | |

[A]Commercially available human thyroglobulin was digested under three different conditions and resulting peptides were separated with liquid chromatography. The peptides were then analyzed using either electrospray ionization tandem mass spectrometry with a linear ion trap mass spectrometer or matrix assisted laser desorption ionization tandem mass spectrometry with a tandem time-of-flight instrument. Peptides were selected based on the total peak area and peak height on both instruments and hydrophobicity near 0.5 or −0.5.
[a]Average mass/charge is listed for the MH+ ion of each peptide.
M# – refers to oxidized methionine (increased mass of 16 Da)
C* – refers to carbamidomethylated cysteine Peptide Analysis and Selection for Antibody Production As shown in TABLE 1, a total of 28 different peptides were detected using both mass spectrometric analysis methods in the tryptic digestion of human thyroglobulin protein (SEQ ID NO:1, shown in FIG. 1). The length of the peptides range from nine amino acid residues up to 29 amino acid residues. TABLE 1 shows the results for the human thyroglobulin peptide resulting from the trypsin digestion as the peak area (as determined from digestions 1-3 analyzed by the ion trap mass spectrometer) or the peak height (as determined from Digestion 1 analyzed by the MALDI-TOF-TOF mass spectrometer). The number of times each peptide sequence was detected is the sum of the number of columns in which the peak area is greater than zero. The peptides were identified with database searching using Xcaliber software and the Sequest searching algorithm (from Thermo Electron, Inc.).

Selection of Peptides for Use as Antigens:

Peptides for use as antigens to raise antibodies for use in a thyroglobulin detection assay, as described in Example 2, were selected based on the total peak area and peak height on both instruments. Peptides were also selected with a preferred hydrophobicity value of between −0.3 to −0.5, or between 0.3 to 0.5.

The three most abundant peptides detected in a trypsin digest of human thyroglobulin are determined using both liquid chromatography-tandem mass spectrometry with a linear ion trap instrument and liquid chromatography-matrix assisted laser desorption ionization-tandem time of flight mass spectrometry, with the desired hydrophobicity values were:

LGDQEFIK (SEQ ID NO:3)(precursor mass 949.50 Da);
VIFDANAPVAVR (SEQ ID NO:2)(precursor mass 1271.71 Da); and
FPLGESFLVAK (SEQ ID NO:5)(precursor mass 1207.67 Da).

These peptides were used as antigens to generate anti-peptide antibodies as described in Example 2.

The three peptides selected for use as antigens (SEQ ID NO:2, SEQ ID NO:3 and SEQ ID NO:5) were selected as the three most reliably abundant peptides on both ESI-ion trap and MALDI-TOF-TOF platforms. The fourth most abundant peptide from Digestion 1 (SEQ ID NO:5) was selected, because the third most abundant peptide (SEQ ID NO:4) was not well recovered when digested without reduction and alkylation or in the presence of serum proteins. The most abundant peptide across platforms and digestions tested, SEQ ID NO:2, was chosen as the internal standard peptide and a stable isotope-labeled peptide was synthesized, as described in more detail in Example 4.

EXAMPLE 2

This example describes the generation of rabbit anti-human thyroglobulin antibodies against selected thyroglobulin peptides for use in an assay to detect human thyroglobulin in a biological sample.

Methods:
Human Thyroglobulin Peptides

The following three peptides from human thyroglobulin described in Example 1 were selected for use as antigens to generate anti-peptide antibodies for use in an assay to detect human thyroglobulin:

LGDQEFIK (SEQ ID NO:3)(precursor mass 949.50 Da);
VIFDANAPVAVR (SEQ ID NO:2)(precursor mass 1271.71 Da); and
FPLGESFLVAK (SEQ ID NO:5)(precursor mass 1207.67 Da).

Conjugation of Peptides

Synthetic peptides were generated for each sequence (SEQ ID NOS:2, 3, and 5) and were conjugated to keyhole limpet hemocyanin (KLH) for immunization of rabbits as follows:

Four different reactions were carried out to conjugate the three peptides to keyhole limpet hemocyanin in order to guarantee presentation of both ends of the selected peptides to the rabbits' immune system. For the two peptides that had lysine at the carboxyl terminus (SEQ ID NO:3 and SEQ ID NO:5), gluteraldehyde was used to conjugate both the peptide amino terminus and the lysine at the carboxyl terminus of the peptides to keyhole limpet hemocyanin (KLH).

Keyhole limpet hemocyanin (KLH, Calbiochem, Gibbstown, N.J.) was suspended in PBS (138 mmol/L, NaCl 2.7 mmol/L, KC: 10 mmol/L, phosphate pH7.4), sonicated and vortexed extensively. The mixture was then dialyzed against PBS (3.5 kDa molecular weight cut-off (MWCO)). The solution was then clarified by centrifugation, and the supernatant was used for peptide conjugation. Peptide (2 mg) dissolved in dimethylsulfoxide was added to the KLH solution. The mixture was then brought up to 1 mmol/L glutaraldehyde and incubated for 16 hours at 4° C. with rotation. The reactions were terminated with a few grains of sodium borohydride.

1-Ethyl-3-[3-dimethylaminopropyl]carbodiimide hydrochloride (EDAC, Sigma, St. Louis, Mo.) was used to conjugate KLH to the carboxyl terminus of SEQ ID NO:2, according to the manufacturer's instructions. Gluteraldehyde was used to conjugate KLH to the amino terminus of SEQ ID NO:2.

Efficiency of conjugation was >65% for each reaction, as assessed by MS/MS quantification of peptide that passed through a 10 kDa MWCO Microcon filter (Milipore, Bedford, Mass.). The peptide-KLH conjugates were combined and used to immunize New Zealand rabbits, as described below.

It will be understood by those of skill in the art that the methods are not limited to the use of KLH, and that other peptides (e.g., ovalbumin, albumin, modified albumin and the like) may be conjugated to SEQ ID NO:2, SEQ ID NO:3, and SEQ ID NO:5 in order to stimulate an immune system of a mammalian subject to generate antibodies that bind to the thyrogloublin peptides.

Immunization

The four conjugation reactions containing the three human thyroglobulin peptides SEQ ID NOS:2, 3, and 5 conjugated with KLH as described above were pooled and used to immunize two New Zealand White rabbits using the standard protocol (Pacific Immunology, Ramona, Calif.). The peptide-conjugate pool containing all three peptides (SEQ ID NOS:2, 3, and 5) was injected superficially into two New Zealand White rabbits with complete Freund's adjuvant. Subsequent booster immunizations were carried out with incomplete Freund's adjuvant for a total of four immunizations. Blood was collected at four-week intervals.

The anti-peptide antibodies were purified from the rabbit serum using the three peptides conjugated to bovine serum albumin (generated as described above, by replacing KLH with bovine serum albumin) cross-linked to a cyanogen bromide-activated sepharose solid phase (Sepharose CNBr-4B GE Lifesciences, Piscataway, N.J.), according to the manufacturer's instructions.

After the anti-peptide antibodies were bound to the solid phase, the sepharose was washed until the wash returned to baseline absorbance (at 280 nm), then the anti-peptide antibodies were eluted with 200 mM glycine pH 2.8 into neutralization buffer. After dialysis in phosphate buffered saline (PBS), the antibodies were stored at 4° C. in the presence of sodium azide (as a preservative).

Coupling Anti-Peptide Antibodies to Paramagnetic Beads

The anti-peptide antibodies were chemically cross-linked to paramagnetic beads (from Invitrogen, Inc.) using activated tosyl groups on the surface of the beads. Following the same procedures as described above for KLH, peptides were conjugated to bovine serum albumin (BSA). Peptide-BSA conjugate was then covalently bound to CNBr-activated Sepharose 4B (0.32 g, GE Lifesciences, Piscataway, N.J.), according to the manufacturer's instructions. Protein concentration of the supernatant confirmed >63% conjugate binding to the beads (Commassie Plus, Pierce, Rockford, Ill.). Peptide-BSA Sepharose conjugate was incubated with 10 mL rabbit serum (16 h, 4° C.). Beads were washed with phosphate buffered saline (PBS) and antibodies were eluted in 870 µl. fractions with 200 mmol/L glycine, pH 2.80 into tubes containing 27 µl 3 mol/L Tris, pH 8.6 and 100 µl 3 mol/L KCL. Peak fractions were pooled. The yield was 2-6 mg per 10 mL rabbit serum. Affinity purified antibody was covalently bound to tosyl-activated Dynal M-280 beads (Invitrogen, Carlsbad, Calif.) according to the manufacturer's instructions. Reactions resulted in 2.3 (symbol for +−) 0.12 (SD) pmol binding sites/µl paramagnetic beads ($2\times10^9$ beads/µL).]

Using a magnet provided by the manufacturer, thyroglobulin peptides in a trypsin digested biological sample that are bound to the anti-peptide antibodies can be isolated from other peptides in the trypsin digest, as described in more detail in EXAMPLE 3.

EXAMPLE 3

This example describes the enrichment and quantitation of thyroglobulin in human serum using the anti-peptide antibodies generated in Example 2.

Methods:

Digestion of Human Serum/Plasma

200 µL of human serum was diluted with 300 µL 100 mM ammonium bicarbonate/0.05% (w:v) Tween 20 (both from Sigma-Aldrich, Inc.). The proteins were reduced with 5 mM dithiothreitol (Bio-Rad, Inc.) for one hour at 37° C. rotating end-over-end. The reduced reactive thiol groups were alkylated with iodoacetamide (from Bio-Rad, Inc.) at room temperature for 30 minutes. The proteins were then digested with 5 µg of modified trypsin (Promega, Inc.) at 37° C. rotating end-over-end for 16 hours, followed by the addition of another 5 µg modified trypsin (Promega, Inc.) at 37° C. rotating end-over-end for four hours.

Enrichment of Selected Thyroglobulin Peptides

20 µL of washed paramagnetic beads with bound anti-peptide antibody raised against thyroglobulin peptides SEQ ID NOS:2, 3, and 5, generated as described in Example 2, were resuspended in the serum digest. The 20 µl of washed paramagnetic beads contained one picomole of antibody binding sites per one microliter of bead suspension (beads were generated according to manufacturer's instructions, from Invitrogen, Inc.). Internal standard peptides, generated as described below, were added to 100 µM each. The mixture was incubated overnight at 4° C. rotating end-over-end. The beads were washed twice with 1 mL 100 mM ammonium bicarbonate and once with 1 mL deionized water. The bound peptides were eluted with 10 µL 2% (v:v) acetic acid, rotating end-over-end for 30 minutes at 37° C.

Detection of Peptides by Liquid Chromatography-Tandem Mass Spectrometry

Using standard C18 reverse phase nanoflow liquid chromatography, peptides were separated from one another during a one hour 0-30% acetonitrile/0.2% formic acid gradient. Eluted peptides were introduced into the mass spectrometer with electrospray ionization and the responses of the endogenous sample peptides normalized to the exogenous internal standard peptides were used to measure the concentration of thyroglobulin in the original human serum sample.

Detection of peptides was carried out using an Applied Biosystems Inc. 4000 Q-TRAP, which is a triple quadrupole instrument capable of specific selection of ions with correct precursor mass in the first quadrupole, ion fragmentation in the gas phase in the second quadrupole, fragment ion selection in the third quadrupole, and ion detection by photomultiplier tube. Ions were introduced to the mass spectrometer using an Eksigent 1D liquid chromatography system and electrospray ionization (from Thermo Electron, Inc.).

Results:

FIG. 2 graphically illustrates the results of the immunoaffinity purification of the thyroglobulin peptide VIFDANAPVAVR (SEQ ID NO:2), demonstrating the ability to detect peak areas to 10 ng/ml of thyroglobulin in a human serum dilutional series.

Prior to using the antibody-based method to immunoaffinity purify peptides from the complex matrix of a human serum digest, experiments were carried out that demonstrated the ability to immunoaffinity purify thyroglobulin peptides diluted in buffer, thyroglobulin peptides spiked into digested human serum, and a digest of serum with thyroglobulin spiked into it (data not shown).

Conclusion:

This example demonstrates that peptides from thyroglobulin can be enriched from a complex mixture of serum/plasma peptides using immunoglobulins that recognize specific thyroglobulin peptides followed by direct identification and quantitation of the thyroglobulin peptides by mass spectrometry.

The use of anti-peptide antibodies to detect thyroglobulin removes the problematic interference of endogenous antibodies. For example, interfering antibodies, either autoantibodies to thyroglobulin itself, or non-specific antibodies to immunoglobulins used in traditional immunoassays, are eliminated during enzymatic digestion. In addition, because thyroglobulin peptide is directly detected using mass spectrometry rather than thyroglobulin protein being detected indirectly using antibodies, this embodiment of the method of the invention solves the problem of standardization and "hook effect" present in traditional immunoassays.

The "hook effect" is characterized by the production of artificially low results from samples that have extraordinarily high concentrations of antigen, far exceeding the concentration of the upper standard in the assay concerned. See, e.g., Hoofnagle and Wener, *CLI* 8:12-14 (2006); and Selby, C., *Ann. Clin. Biochem.* 36:704-721 (1999). For these reasons, this method may be used as a reference method for the detection of thyroglobulin in biological specimens that can be used as a reference standard for comparison to results of other methods of detection of thyroglobulin and thereby improve the accuracy of detection of residual, recurrent or metastatic disease in patients afflicted with thyroid cancer.

EXAMPLE 4

This example describes another experiment demonstrating the enrichment and quantitation of thyroglobulin in human serum using the anti-peptide antibodies generated in Example 2.

Methods:

Internal Standard Peptide:

A stable-isotope labeled internal standard peptide (VIFDANAPV*AVR)(SEQ ID NO:2) was synthesized, where V* represents $^{13}C_5$, $^{14}N$-labeled valine, was synthesized by Anaspec (San Jose, Calif.). Isotopic purity of the peptide was 99.9%.

Human Samples:

All human samples were used in accordance with guidelines established by the Human Subjects Committee of the University of Washington.

Digestion of Human Serum/Plasma:

100 µl of human serum was diluted with 400 µl of 100 mM $NH_4HCO_3$, 0.005% Tween 20 (w:v) and reduced with 5 mM DTT for 60 minutes at 37° C., with rotation. The samples were alkylated in the dark with 15 mM iodoacetamide (15 to 120 minutes) and digested in two steps: first with 4.5 µg trypsin for four hours at 37° C., with rotation); and second with 4.5 µg trypsin for 16 hours at 37° C., with rotation. 20 µl of washed paramagnetic beads with anti-peptide antibody raised against thyroglobulin peptides SEQ ID NOS:2, 3, and 5, (containing 46 pmol of peptide binding sites) generated as described in Example 2, were resuspended in the serum digest. 10 µl of internal standard peptide (15 nmol/L), synthesized as described above, was also added to the serum digest, followed by incubation for 16 hours at 4° C.

The beads were washed twice with 500 µl 100 mmol/L ammonium acetate and then washed twice with 500 µl water. Bound Tg peptides were eluted with 15 µl 2% acetic acid (incubated for 1-2 hours at room temperature, with rotation). Human serum calibrators were analyzed in parallel with clinical specimens.

Liquid Chromatography-Tandem Mass Spectrometry:

Eluted peptides (6 µl) were loaded in duplicate onto a peptide trapping column (1 mm×5 mm, Acclaim PepMap100 C18, Dionex, Sunnyvale, Calif.) and washed with 100% buffer A (2% acetonitrile, 0.1% formic acid in water) before being eluted onto a 0.15×150 mm 5 µm 200 Å C18AQ analytical column (Micron, Auburn, Calif.), with a gradient to 35% buffer B (98% acetonitrile, 0.1% formic acid) over eight minutes at 1,000 nL/min using a Tempo 1D-plus nanoflow liquid chromatography system.

Peptides were analyzed in multiple reaction monitoring mode (MRM) with an Applied Biosystems API 4000 QTRAP using the following transitions:

636.4/1059.6, 636.4/541.3 for SEQ ID NO:2;
475.3/836.4, 475.3/779.4 for SEQ ID NO:3;
604.3/850.5, 604.3/963.5 for SEQ ID NO:5;
639.8/1065.6, 639.4/547.3 for the internal standard peptide.

Peak areas for the transitions were summed for each peptide. Endogenous peptide peak areas were normalized to the peak area of the internal standard peptide.

Quantification of International Tg Reference Material:

The international certified reference material BCR-457 was generated in 1992 from pooled human thyroglobulin isolated from cadaveric thyroid tissue and has been used to provide traceable commercial immunoassays (Feldt-Rasmussen, U., et al., *Ann Biol Clin* 54:343-8 (1996)). The concentration of thyroglobulin in this reference material has been quantified using the Lowry method, which has been shown to be less precise than methods of direct detection (Barr, J. R., et al., *Clin Chem* 42:1676-82 (1996)).

With the stable-isotope labeled internal standard (VIFDANAPV*AVR)(SEQ ID NO:2) where V* represents $^{13}C_5$, $^{14}N$-labeled valine), the amount of thyroglobulin in the international Tg reference material was quantified as follows.

After reduction and alkylation with iodoacetamide, triplicate dilution series of the certified reference preparation of Tg (BCR-457, Sigma, St. Louis, Mo.) were digested for two hours at 37° C. using 0.5 µg sequencing grade modified trypsin in 0.1% Rapigest (Waters, Milford, Mass.). Peptides were then lyophilized and reconstituted in 5% acetonitrile, 0.1% formic acid. Suspended peptides were mixed with an equal volume of isotope-labeled internal standard peptide (15 nmol/L) and analyzed with LC-MS/MS.

Figure 3:
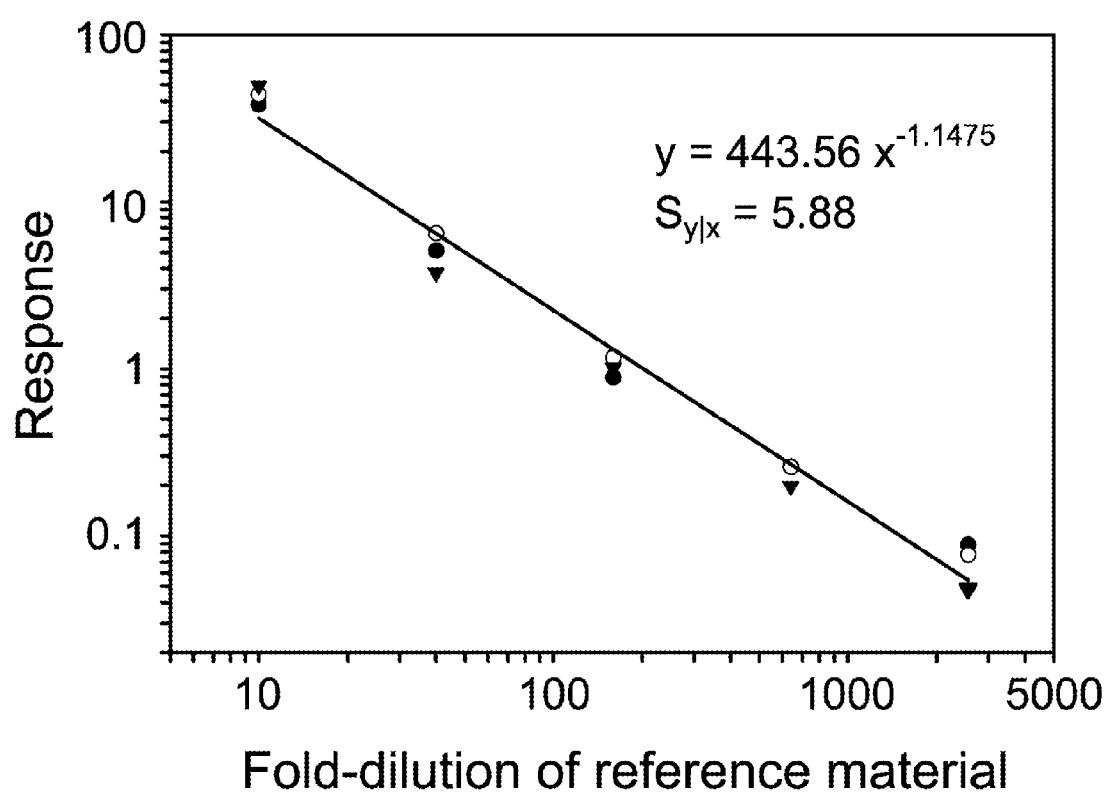
FIG. 3 graphically illustrates the results of the experiment carried out to quantify the amount of thyroglobulin in the international certified reference material (BCR-457), as described in Example 4.

Results:

FIG. 3 graphically illustrates the results of the experiment carried out to quantify the amount of thyroglobulin in the international certified reference material (BCR-457). As described above, triplicate dilutions of the certified reference material were digested with trypsin and the concentration of SEQ ID NO:2 peptide was determined from the ratio of endogenous to spiked internal standard peptide. Each replicate dilution series in FIG. 3 is represented with different symbols. The curve representing the average of the data points was fit to an equation of the form $y=Ax^n$, which was used to determine the dilution necessary to achieve a response of 1.0 (i.e., solving for the dilution (x) where the response (y) equals 1.0). Data shown in FIG. 3 are representative of three independent experiments.

As shown in FIG. 3, the concentration of thyroglobulin in the international reference material BCR-457 using the methods described in this experiment was determined to be 317±7 µg/mL (mean+/SD; N=3), which is very similar to that previously reported for the BCR-457 preparation (324±18 µg/mL).

The goal of this study was to quantify endogenous serum thyroglobulin (Tg) using LC-MS/MS to directly detect specific peptides in tryptic digests of human serum. Polyclonal antibodies were generated in rabbits and covalently bound to a paramagnetic solid phase to enrich Tg peptides from proteolytic digests. Stable-isotope labeled internal standard peptide was included in the immunoaffinity enrichment to help control variability due to sample handling and mass spectrometer performance, and external standards were used to calibrate the response of the endogenous analyte.

With regard to the trypsin digestion, in order to avoid solid phase extraction, which could increase variability due to added specimen manipulation, an alternative approach was used by adding the non-ionic detergent Tween 20 to help denature proteins and to provide stringency in the immunoaffinity purification step. After testing various concentrations of Tween 20, it was determined that reduction and alkylation of 20% serum led to a cloudy solution that was reproducibly cleared with trypsin in the presence of 0.005% (w:v) Tween 20, but not without. Therefore, Tween 20 was included in the trypsin digestions.

It was also determined that sequencing grade trypsin was the only preparation capable of clarifying all human samples tested (N=10).

LC-MS/MS Analysis of Endogenous Thyroglobulin

Enriched Tg peptides were bound to a C18 trapping column and washed prior to being eluted with an acetonitrile gradient and resolved on an analytical column. FIGS. 4A-4G illustrate the ion current chromatograms for the internal standard and the endogenous peptides. Immunoaffinity purified peptides were first loaded onto a peptide trapping column before being resolved with a C18 analytical column, ionized using microelectrospray ionization, and analyzed using multiple reaction monitoring (MRM). Elution profiles of peptides purified from a digest of human serum are shown for each peptide in FIGS. 4A, 4C, 4E, and 4G. Fragment ion spectra were collected in the linear ion trap of the mass spectrometer simultaneously with the collection of MRM data, and are shown for each peptide in FIGS. 4B, 4D, 4F, and 4H.

Figures 4A, 4B:
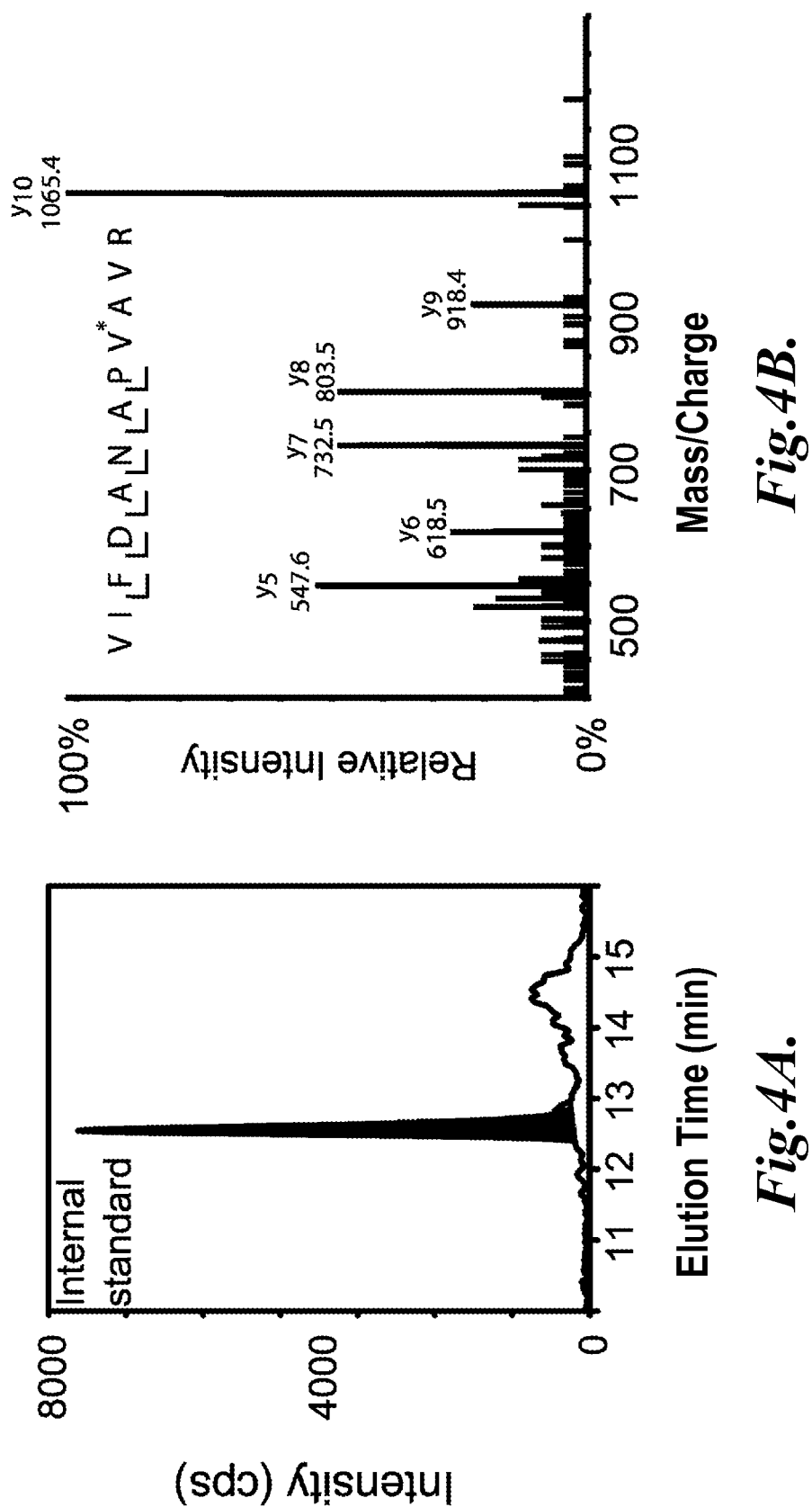
FIG. 4A graphically illustrates the elution profile of the internal standard (VIFDANAPV*AVR)(SEQ ID NO:2) where V* represents $^{13}C_5$, $^{14}N$-labeled valine)
FIG. 4B graphically illustrates the fragment ion spectra collected in the linear ion trap of the mass spectrometer for the internal standard (VIFDANAPV*AVR)(SEQ ID NO:2) where V* represents $^{13}C_5$, $^{14}N$-labeled valine)

FIG. 4A graphically illustrates the elution profile of the internal standard (VIFDANAPV*AVR)(SEQ ID NO:2) where V* represents $^{13}C_5$, $^{14}N$-labeled valine).

FIG. 4B graphically illustrates the fragment ion spectra collected in the linear ion trap of the mass spectrometer for the internal standard (VIFDANAPV*AVR) (SEQ ID NO:2) where V* represents $^{13}C_5$, $^{14}N$-labeled valine).

Figure 4D:
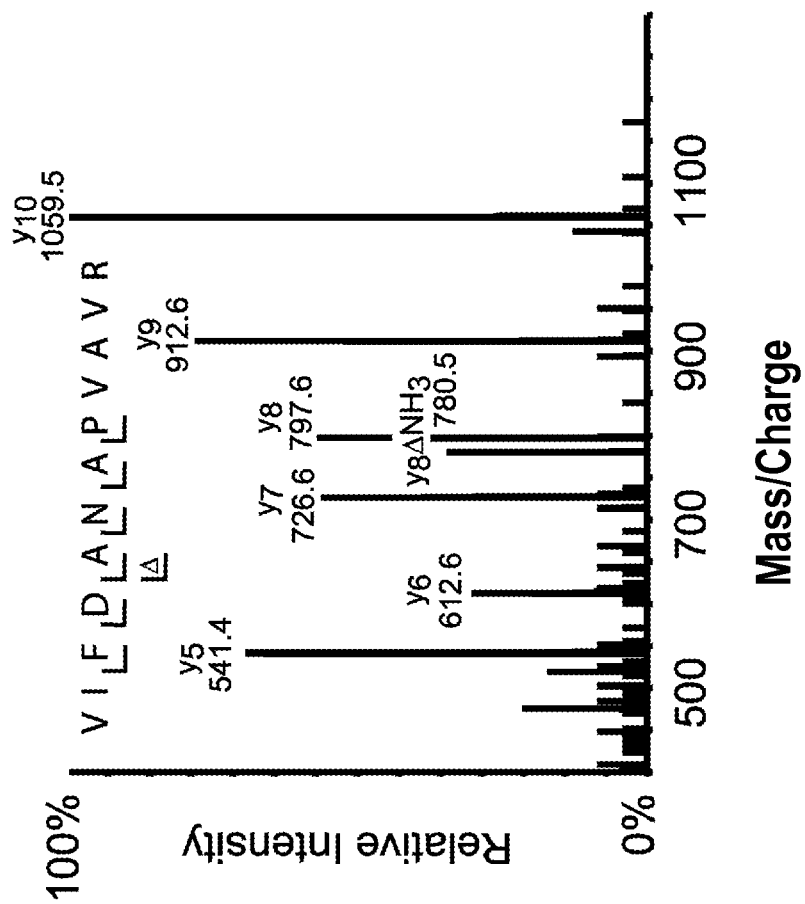
FIG. 4D graphically illustrates the fragment ion spectra collected in the linear ion trap of the mass spectrometer for the endogenous peptide SEQ ID NO:2.
Figure 4C:
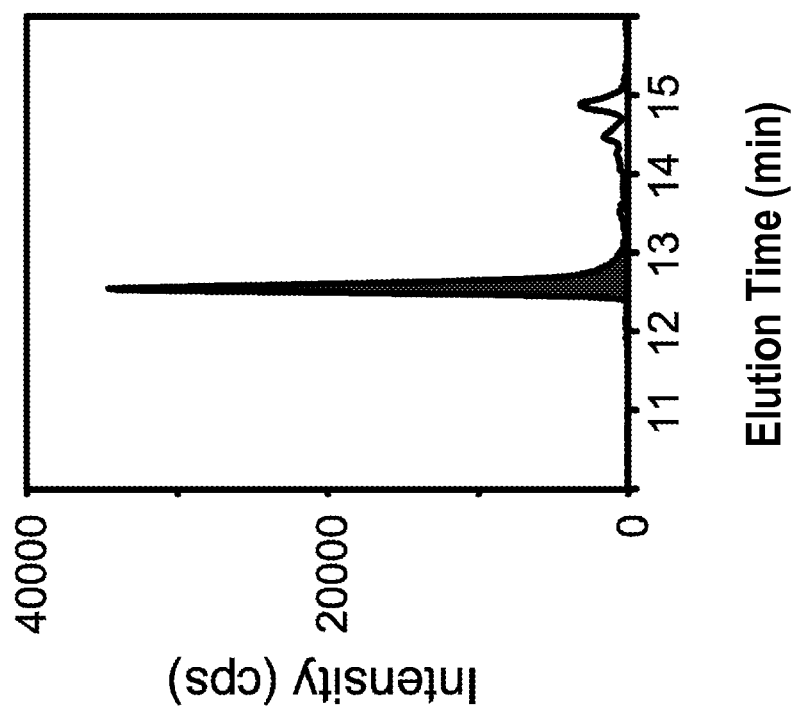
FIG. 4C graphically illustrates the elution profile of endogenous peptide SEQ ID NO:2 purified from a digest of human serum.

FIG. 4C graphically illustrates the elution profile of endogenous peptide SEQ ID NO:2 purified from a digest of human serum.

FIG. 4D graphically illustrates the fragment ion spectra collected in the linear ion trap of the mass spectrometer for the endogenous peptide SEQ ID NO:2.

Figure 4F:
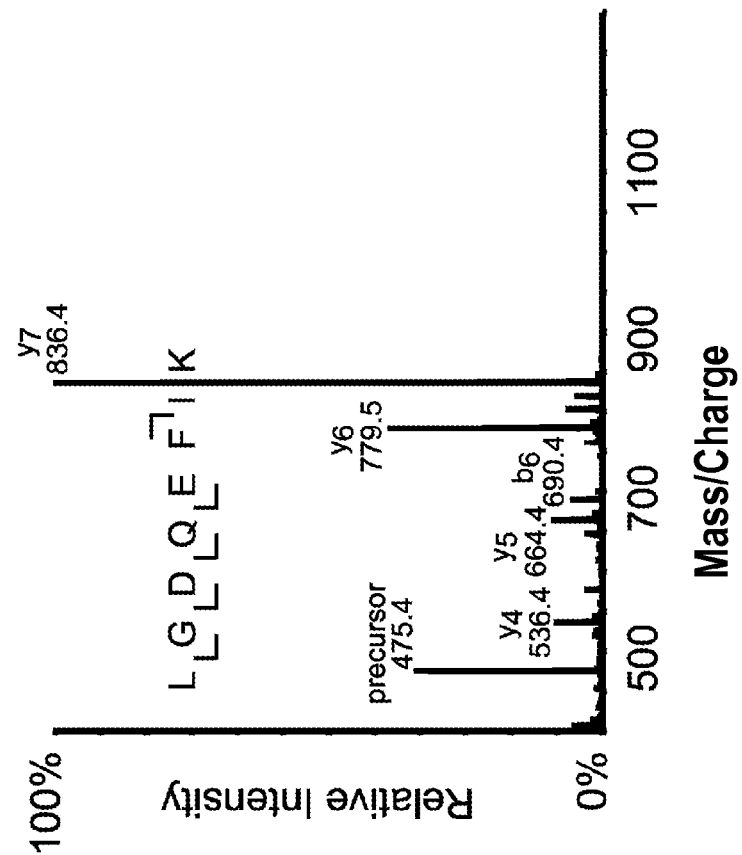
FIG. 4F graphically illustrates the fragment ion spectra collected in the linear ion trap of the mass spectrometer for the endogenous peptide SEQ ID NO:3.
Figure 4E:
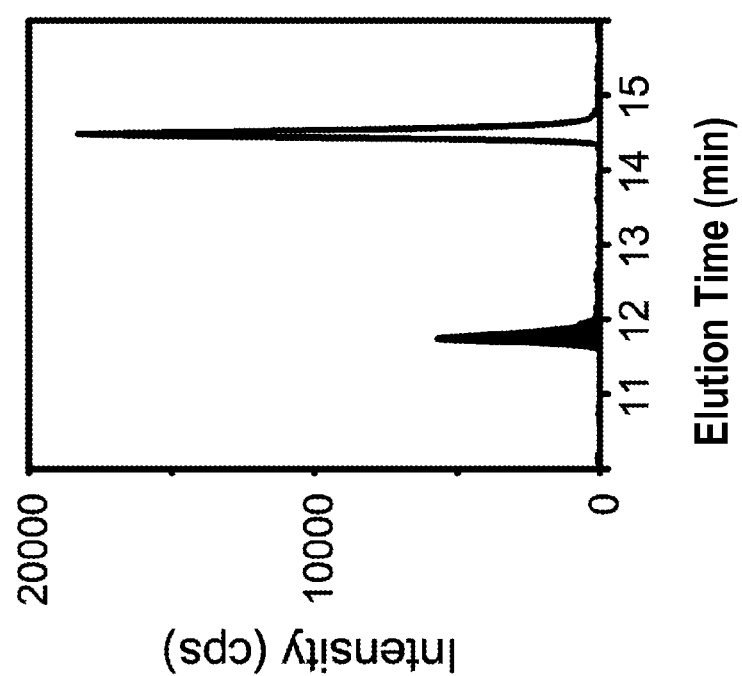
FIG. 4E graphically illustrates the elution profile of endogenous peptide SEQ ID NO:3 purified from a digest of human serum.

FIG. 4E graphically illustrates the elution profile of endogenous peptide SEQ ID NO:3 purified from a digest of human serum.

FIG. 4F graphically illustrates the fragment ion spectra collected in the linear ion trap of the mass spectrometer for the endogenous peptide SEQ ID NO:3.

Figures 4G, 4H:
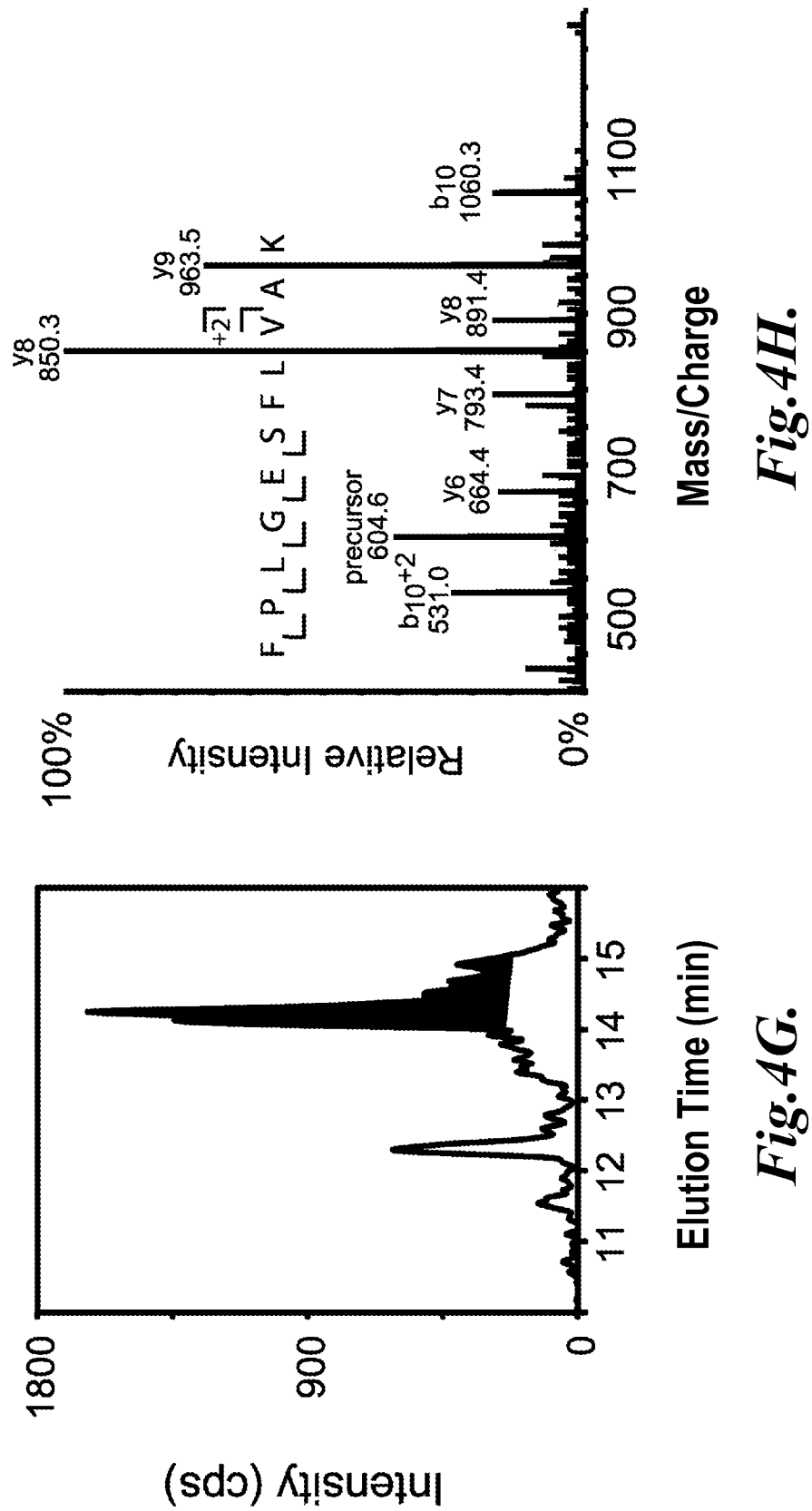
FIG. 4G graphically illustrates the elution profile of endogenous peptide SEQ ID NO:5 purified from a digest of human serum.
FIG. 4H graphically illustrates the fragment ion spectra collected in the linear ion trap of the mass spectrometer for the endogenous peptide SEQ ID NO:5, as described in Example 4.

FIG. 4G graphically illustrates the elution profile of endogenous peptide SEQ ID NO:5 purified from a digest of human serum.

FIG. 4H graphically illustrates the fragment ion spectra collected in the linear ion trap of the mass spectrometer for the endogenous peptide SEQ ID NO:5.

As shown in FIG. 4C (SEQ ID NO:2), FIG. 4E (SEQ ID NO:3) and FIG. 4G (SEQ ID NO:5), peptides SEQ ID NO:2 and SEQ ID NO:3 elute earlier than peptide SEQ ID NO:5 and have a significantly narrower peak width.

As shown in FIGS. 4B, 4D, 4F, and 4H, tandem mass spectra can be collected in parallel with the MRM transitions using the linear ion trap of the 4000 Q-TRAP mass spectrometer. Therefore, these results demonstrate that interpretable MS/MS spectra can be acquired for each peptide tested in serum samples with as little as 100 ng/mL endogenous Tg.

EXAMPLE 5

This example describes an experiment to determine the performance of the three peptides (SEQ ID NO:2, SEQ ID NO:3, and SEQ ID NO:5) in an assay to detect Tg in human serum.

Methods:

To further determine the performance of the three peptides (SEQ ID NO:2, SEQ ID NO:3 and SEQ ID NO:5) in an assay to detect Tg in human serum, human serum containing 319 ng/mL endogenous thyroglobulin was diluted serially with serum that contained no Tg. The samples were reduced, alkylated and digested with trypsin, as described in Example 4. The resulting peptides were enriched for thyroglobulin peptides using paramagnetic beads coated with antibodies to Tg peptides, as described in Example 4. Peptides eluted from the anti-peptide beads were analyzed with LC-MS/MS, as described in Example 4.

Figure 5A:
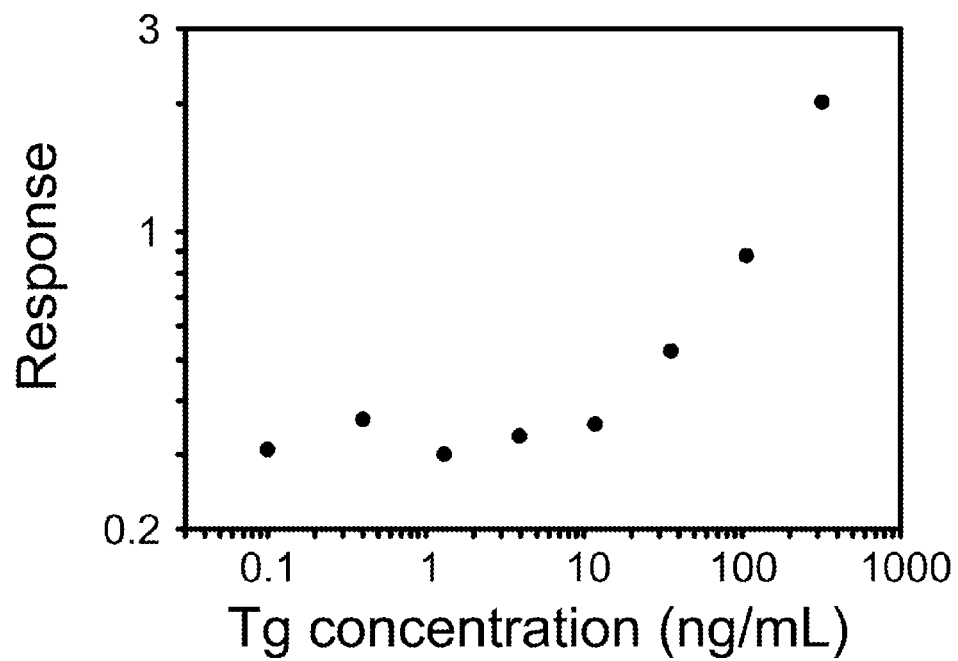
FIG. 5A graphically illustrates the response (peak area of endogenous peptide SEQ ID NO:2/peak area internal standard peptide) detected in a dilution series of a human serum sample containing 319 ng/mL Tg, as described in Example 5.
Figure 5B:
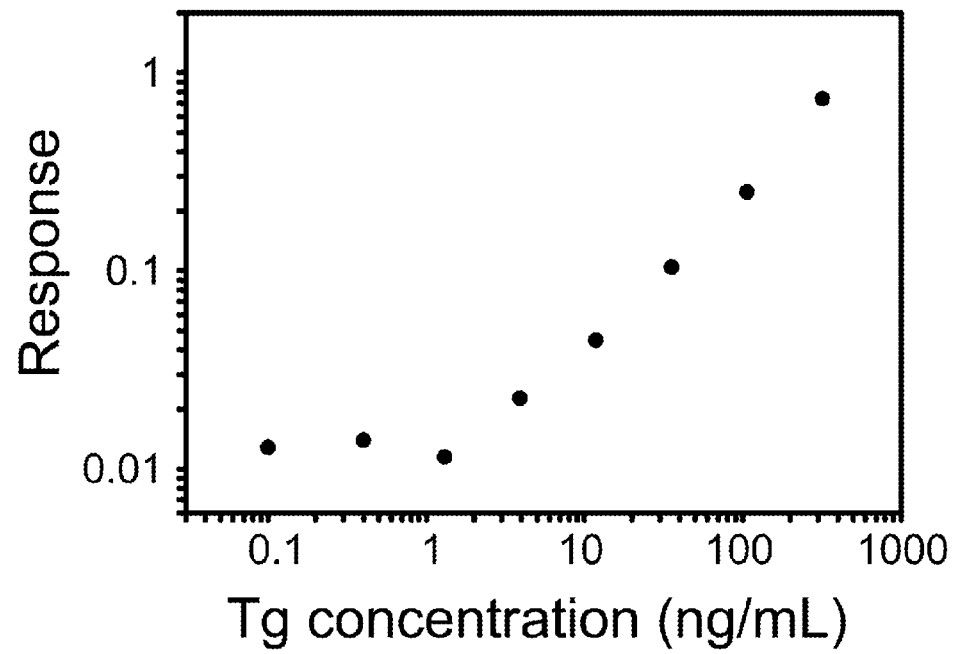
FIG. 5B graphically illustrates the response (peak area of endogenous peptide SEQ ID NO:3/peak area internal standard peptide) detected in a dilution series of a human serum sample containing 319 ng/mL Tg, as described in Example 5.
Figure 5C:
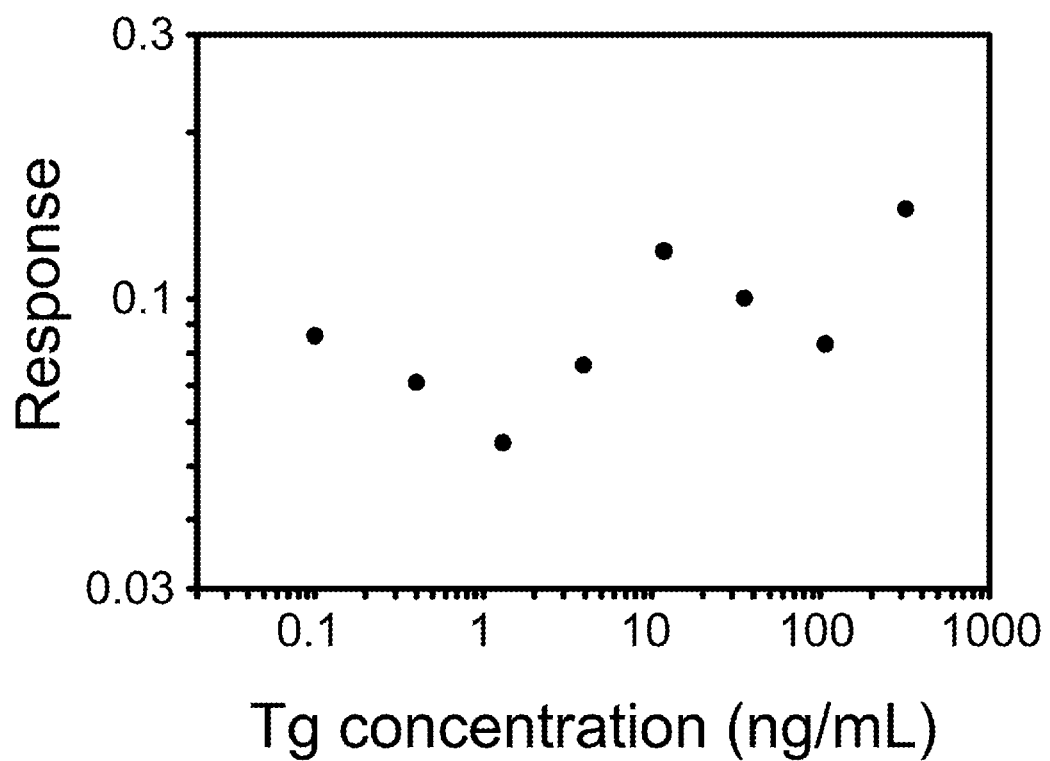
FIG. 5C graphically illustrates the response (peak area of endogenous peptide SEQ ID NO:5/peak area internal standard peptide) detected in a dilution series of a human serum sample containing 319 ng/mL Tg, as described in Example 5.

Results:

FIG. 5A-5C graphically illustrate the response (peak area of endogenous peptide/peak area internal standard peptide) for each peptide (FIG. 5A: SEQ ID NO:2; FIG. 5B: SEQ ID NO:3; FIG. 5C: SEQ ID NO:5), detected in a dilution series of a human serum sample containing 319 ng/mL Tg. The internal standard peptide (VIFDANAPV*AVR)(SEQ ID NO:2) where V* represents $^{13}C_5$, $^{14}N$-labeled valine, is chemically identical to SEQ ID NO:2 peptide and differs only in mass. As shown in FIGS. 5A-5C, the three peptides (SEQ ID NO:2, SEQ ID NO:3, and SEQ ID NO:5) behaved differently.

When analyzed for peak areas only (data not shown), peptide SEQ ID NO:3 performed the best of the three peptides, with a minimal detectable concentration of 3 ng/mL. Peptide SEQ ID NO:2 had a significant background signal, likely resulting from a peptide that populated antibody binding sites after affinity purification of the antibody, and was different from the zero calibrator at 30 ng/mL. Peptide SEQ ID NO:5 also included high background signal, suffered from greater variability, and had a minimal detectable concentration of 100 ng/mL.

As described above, internal standard peptide was added after digestion to control for variability in the volume of immunoglobulin-coated beads added and to control for variability in sample volume injection and ionization. As shown in FIGS. 5A-5C, after normalization to the internal standard peptide, the responses of peptide SEQ ID NO:2 and the peptide SEQ ID NO:3 had similar characteristics to their respective peak areas, but the response of peptide SEQ ID NO:5 was more erratic.

Discussion of Results

Of the three peptides tested in this experiment, peptide SEQ ID NO:3 allowed for the most sensitive detection of endogenous thyroglobulin. As described in Example 6, good intra-assay precision was demonstrated for peptide SEQ ID NO:3 at 3.8 ng/mL (12 fmol/L) in human serum.

With regard to the other two peptides, it appears that peptide SEQ ID NO:5 may have elicited a poorer antibody response as compared with the other peptides tested, as evidenced by its high limit of detection. Although peptide SEQ ID NO:2 was the most abundant peptide detected by digesting purified human thyroglobulin, as shown in TABLE 1, it was determined that during the generation of the albumin-peptide conjugate used for affinity purification, this peptide non-covalently associated with albumin and bound to CNBr-activated beads directly. The ester linkage formed between conjugate and bead is known to slowly hydrolyze over time, leading to background interference. It is believed that the use of other strategies to generate affinity-purified, highly specific polyclonal antibodies, which are known to those of skill in the art, would alleviate the problem encountered with this peptide. Alternatively, the use of monoclonal antibodies to the peptides would not require affinity purification, and would therefore eliminate the problems related to the affinity purification process.

EXAMPLE 6

This example describes the use of peptide SEQ ID NO:3 for quantitation of Tg in human serum specimens.

Methods:

Given the superior performance of peptide SEQ ID NO:3, it was used for quantitation in subsequent human serum specimens using the peptide response calculated as the peak area of analyte divided by the peak area of the internal standard.

Human serum calibrators were chosen after comparing thyroglobulin spiked into albumin, various dilutions of fetal calf serum, and 100% human serum. It was determined that human calibrators provided the least bias as compared with immunoassay (data not shown). The human serum calibrators used in this experiment were human serum samples (known to be negative of thyroglobulin) with purified thyroglobulin (SEQ ID NO:1) spiked into the serum at known concentrations, or the concentration of spiked in thyroglobulin was determined by another methodology using known immunoassay detection techniques.

Human calibrators were analyzed in parallel with other human serum specimens (0, 2, 5, and 20 ng/mL). The assay for Tg using SEQ ID NO:3 had an intra-assay precision of 13.7% at 22.3 ng/mL Tg, 22.5% at 5.5 ng/mL Tg, and 21.4% at 3.8 ng/mL Tg. Interassay precision was 17.4% at 6.0 ng/mL Tg. The lower limit of detection of Tg, defined as the concentration corresponding to mean+2 SD of the zero calibrator, was 2.6 ng/mL Tg. At 5.5 ng/mL Tg, the mean signal-to-noise ratio was 5.7 (95% CI 3.0-8.3).

Recovery of thyroglobulin spiked into five Tg negative human serum samples at 21.6 ng/mL ranged from 85.0% to 99.6% (mean±SD was 93.0±5.4%). As calculated using peak area determinations, the mean carryover was 0.8%±0.8% (SD). Using the above-described configuration, 14 samples and four calibrators can be analyzed at a time in a three day time period.

Figure 6A:
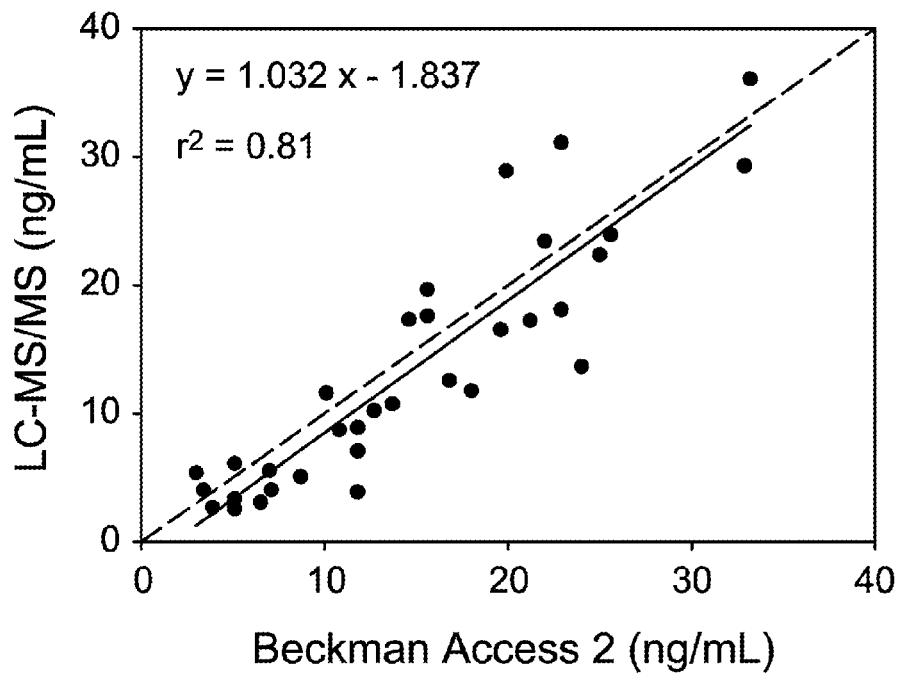
FIG. 6A graphically illustrates a comparison between the Tg detection results obtained from a Beckman Access 2 assay x-axis) and the results obtained from the immunoaffinity enrichment and LC-MS/MS assay for peptide SEQ ID NO:3 (y-axis), as described in Example 6.
Figure 6B:
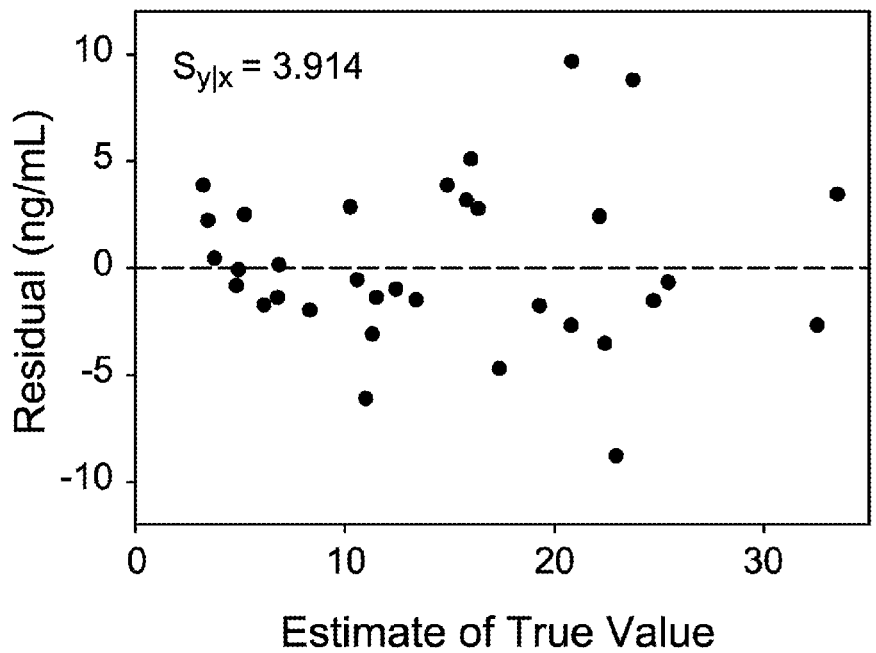
FIG. 6B graphically illustrates the residuals of each data point from the regression line shown in FIG. 6A, wherein the standard error of the residuals ($S_{y/x}$) was determined to be 3.914, as described in Example 6.

The assay with peptide SEQ ID NO:3 was then compared to a currently available immunoassay. To evaluate comparability, 33 samples were analyzed that had been previously quantified using the Beckman Access 2 assay for Tg (Beckman Coulter, Fullerton, Calif.), spanning a range of 3.0 ng/mL to 33.2 ng/mL Tg. The results obtained using the Beckman Access 2 Tg assay were compared with the results using immunoaffinity purification of peptide SEQ ID NO:3 from tryptic digests with external calibration. FIG. 6A graphically illustrates a comparison between the Beckman Access 2 assay results x-axis) and the results obtained from the LC-MS/MS assay with peptide SEQ ID NO:3 (y-axis). As shown in FIG. 6A, the equation of the Deming regression (Analyse-It, Leeds, England, UK) had a slope (95% confidence interval) of 1.032 (0.850-1.216) and an intercept of −1.837 (−4.929-1.256). The Pearson correlation coefficient ($r^2$) was 0.81. The residuals of each data point from the regression line shown in FIG. 6A are shown in FIG. 6B, wherein the standard error of the residuals ($S_{y/x}$) was 3.914.

Therefore, it has been demonstrated that the immunoaffinity enrichment and LC-MS/MS assay performs well in comparison with an established immunoassay for Tg detection, even at the low picomolar range in human serum. This result is significant in that this level of detection has not been demonstrated for LC-MS/MS quantification of Tg or other endogenous proteins in human serum or plasma. For example, previous attempts at the quantification of proteins in endogenous human serum have included the direct detection of peptides from Zn-α2 glycoprotein, which was successfully quantified with a sensitivity of ~3 μg/mL (90 nmol/L)(Sapin, R., *Clin Chem* 53:810-2 (2007)). Therefore, this study is the first time, as far as is known, in which a peptide immunoaffinity purification method has been successfully used to measure an endogenous low abundance protein in human serum, such as Tg, with a sensitivity of 9 pmol/L.

It is also important to note that trypsin digestion has an inherent advantage over immunoassay in that it destroys endogenous antibody interferences due either to anti-analyte autoantibodies or non-specific heterophilic antibodies. In addition, by directly detecting an analyte such as an endogenous peptide in reference to a stable-isotope labeled internal standard peptide, mass spectrometry has the advantage of being more easily standardized across laboratories, especially when a standard reference preparation is already available, such as is the case for Tg. Therefore, it is believed that the methods of detecting low abundance Tg in serum provides an alternative diagnostic approach to the methods currently available that are plagued by interference and lack of standardization.

While illustrative embodiments have been illustrated and described, it will be appreciated that various changes can be made therein without departing from the spirit and scope of the invention.

The embodiments of the invention in which an exclusive property or privilege is claimed are defined as follows:

1. A composition comprising at least one synthetic or recombinant thyroglobulin peptide consisting of SEQ ID NO:2, SEQ ID NO:3, or SEQ ID NO:5.

2. The composition of claim 1, wherein the composition comprises SEQ ID NO:2 and SEQ ID NO:3.

3. The composition of claim 2, wherein the composition further comprises SEQ ID NO:5.

4. The composition of claim 1, wherein the at least one synthetic or recombinant thyroglobulin peptide is conjugated to a peptide that stimulates an immune system of a mammalian subject.

5. The composition of claim 1, wherein the at least one peptide is conjugated to keyhole limpet hemocyanin.

6. The composition of claim 1, wherein the at least one synthetic or recombinant thyroglobulin peptide consists of SEQ ID NO:2.

7. The composition of claim 1, wherein the at least one synthetic or recombinant thyroglobulin peptide consists of SEQ ID NO:3.

8. The composition of claim 1, wherein the at least one synthetic or recombinant thyroglobulin peptide consists of SEQ ID NO:5.

9. The composition of claim 1, wherein the composition further comprises an adjuvant for inducing an immune response in a mammalian subject.

10. A composition comprising at least one thyroglobulin peptide consisting of SEQ ID NO:2, SEQ ID NO:3, or SEQ ID NO:5, wherein the at least one peptide is conjugated to keyhole limpet hemocyanin.

11. The composition of claim 10, wherein the composition further comprises an adjuvant for inducing an immune response in a mammalian subject.

* * * * *

UNITED STATES PATENT AND TRADEMARK OFFICE
CERTIFICATE OF CORRECTION

| | | |
|---|---|---|
| PATENT NO. | : 7,807,172 B2 | Page 1 of 1 |
| APPLICATION NO. | : 12/139382 | |
| DATED | : October 5, 2010 | |
| INVENTOR(S) | : A. N. Hoofnagle et al. | |

It is certified that error appears in the above-identified patent and that said Letters Patent is hereby corrected as shown below:

Title Page, Item (57) Abstract "regent" should read --reagent--

Signed and Sealed this
Eighth Day of February, 2011

David J. Kappos
*Director of the United States Patent and Trademark Office*

SEQUENCE LISTING

<160> NUMBER OF SEQ ID NOS: 29

<210> SEQ ID NO 1
<211> LENGTH: 2768
<212> TYPE: PRT
<213> ORGANISM: Homo sapiens

<400> SEQUENCE: 1

Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln Gln Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
        195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

-continued

```
Gln Gly Arg Glu Leu Ala Glu Thr Gly Leu Glu Leu Leu Asp Glu
                245                 250                 255

Ile Tyr Asp Thr Ile Phe Ala Gly Leu Asp Leu Pro Ser Thr Phe Thr
                260                 265                 270

Glu Thr Thr Leu Tyr Arg Ile Leu Gln Arg Arg Phe Leu Ala Val Gln
                275                 280                 285

Ser Val Ile Ser Gly Arg Phe Arg Cys Pro Thr Lys Cys Glu Val Glu
        290                 295                 300

Arg Phe Thr Ala Thr Ser Phe Gly His Pro Tyr Val Pro Ser Cys Arg
305                 310                 315                 320

Arg Asn Gly Asp Tyr Gln Ala Val Gln Cys Gln Thr Glu Gly Pro Cys
                325                 330                 335

Trp Cys Val Asp Ala Gln Gly Lys Glu Met His Gly Thr Arg Gln Gln
                340                 345                 350

Gly Glu Pro Pro Ser Cys Ala Glu Gly Gln Ser Cys Ala Ser Glu Arg
            355                 360                 365

Gln Gln Ala Leu Ser Arg Leu Tyr Phe Gly Thr Ser Gly Tyr Phe Ser
        370                 375                 380

Gln His Asp Leu Phe Ser Ser Pro Glu Lys Arg Trp Ala Ser Pro Arg
385                 390                 395                 400

Val Ala Arg Phe Ala Thr Ser Cys Pro Pro Thr Ile Lys Glu Leu Phe
                405                 410                 415

Val Asp Ser Gly Leu Leu Arg Pro Met Val Glu Gly Gln Ser Gln Gln
            420                 425                 430

Phe Ser Val Ser Glu Asn Leu Leu Lys Glu Ala Ile Arg Ala Ile Phe
        435                 440                 445

Pro Ser Arg Gly Leu Ala Arg Leu Ala Leu Gln Phe Thr Thr Asn Pro
    450                 455                 460

Lys Arg Leu Gln Gln Asn Leu Phe Gly Gly Lys Phe Leu Val Asn Val
465                 470                 475                 480

Gly Gln Phe Asn Leu Ser Gly Ala Leu Gly Thr Arg Gly Thr Phe Asn
                485                 490                 495

Phe Ser Gln Phe Gln Gln Leu Gly Leu Ala Ser Phe Leu Asn Gly
            500                 505                 510

Gly Arg Gln Glu Asp Leu Ala Lys Pro Leu Ser Val Gly Leu Asp Ser
        515                 520                 525

Asn Ser Ser Thr Gly Thr Pro Glu Ala Ala Lys Lys Asp Gly Thr Met
    530                 535                 540

Asn Lys Pro Thr Val Gly Ser Phe Gly Phe Glu Ile Asn Leu Gln Glu
545                 550                 555                 560

Asn Gln Asn Ala Leu Lys Phe Leu Ala Ser Leu Leu Glu Leu Pro Glu
                565                 570                 575

Phe Leu Leu Phe Leu Gln His Ala Ile Ser Val Pro Glu Asp Val Ala
                580                 585                 590

Arg Asp Leu Gly Asp Val Met Glu Thr Val Leu Ser Ser Gln Thr Cys
            595                 600                 605

Glu Gln Thr Pro Glu Arg Leu Phe Val Pro Ser Cys Thr Thr Glu Gly
        610                 615                 620

Ser Tyr Glu Asp Val Gln Cys Phe Ser Gly Glu Cys Trp Cys Val Asn
625                 630                 635                 640

Ser Trp Gly Lys Glu Leu Pro Gly Ser Arg Val Arg Gly Gly Gln Pro
                645                 650                 655
```

```
Arg Cys Pro Thr Asp Cys Glu Lys Gln Arg Ala Arg Met Gln Ser Leu
            660                 665                 670

Met Gly Ser Gln Pro Ala Gly Ser Thr Leu Phe Val Pro Ala Cys Thr
            675                 680                 685

Ser Glu Gly His Phe Leu Pro Val Gln Cys Phe Asn Ser Glu Cys Tyr
            690                 695                 700

Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
            740                 745                 750

Pro Thr Leu Ser Asp Thr Tyr Ile Pro Gln Cys Ser Thr Asp Gly Gln
            755                 760                 765

Trp Arg Gln Val Gln Cys Asn Gly Pro Pro Glu Gln Val Phe Glu Leu
            770                 775                 780

Tyr Gln Arg Trp Glu Ala Gln Asn Lys Gly Gln Asp Leu Thr Pro Ala
785                 790                 795                 800

Lys Leu Leu Val Lys Ile Met Ser Tyr Arg Glu Ala Ala Ser Gly Asn
                805                 810                 815

Phe Ser Leu Phe Ile Gln Ser Leu Tyr Glu Ala Gly Gln Gln Asp Val
            820                 825                 830

Phe Pro Val Leu Ser Gln Tyr Pro Ser Leu Gln Asp Val Pro Leu Ala
            835                 840                 845

Ala Leu Glu Gly Lys Arg Pro Gln Pro Arg Glu Asn Ile Leu Leu Glu
            850                 855                 860

Pro Tyr Leu Phe Trp Gln Ile Leu Asn Gly Gln Leu Ser Gln Tyr Pro
865                 870                 875                 880

Gly Ser Tyr Ser Asp Phe Ser Thr Pro Leu Ala His Phe Asp Leu Arg
                885                 890                 895

Asn Cys Trp Cys Val Asp Glu Ala Gly Gln Glu Leu Glu Gly Met Arg
            900                 905                 910

Ser Glu Pro Ser Lys Leu Pro Thr Cys Pro Gly Ser Cys Glu Glu Ala
            915                 920                 925

Lys Leu Arg Val Leu Gln Phe Ile Arg Glu Thr Glu Glu Ile Val Ser
            930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
                965                 970                 975

Pro Pro Arg Glu Ala Phe Ala Gln Phe Leu Arg Gly Ser Asp Tyr
            980                 985                 990

Ala Ile Arg Leu Ala Ala Gln Ser Thr Leu Ser Phe Tyr Gln Arg Arg
            995                 1000                1005

Arg Phe Ser Pro Asp Asp Ser Ala Gly Ala Ser Ala Leu Leu Arg
            1010                1015                1020

Ser Gly Pro Tyr Met Pro Gln Cys Asp Ala Phe Gly Ser Trp Glu
            1025                1030                1035

Pro Val Gln Cys His Ala Gly Thr Gly His Cys Trp Cys Val Asp
            1040                1045                1050

Glu Lys Gly Gly Phe Ile Pro Gly Ser Leu Thr Ala Arg Ser Leu
            1055                1060                1065
```

```
Gln Ile Pro Gln Cys Pro Thr Thr Cys Glu Lys Ser Arg Thr Ser
    1070            1075                1080

Gly Leu Leu Ser Ser Trp Lys Gln Ala Arg Ser Gln Glu Asn Pro
    1085            1090                1095

Ser Pro Lys Asp Leu Phe Val Pro Ala Cys Leu Glu Thr Gly Glu
    1100            1105                1110

Tyr Ala Arg Leu Gln Ala Ser Gly Ala Gly Thr Trp Cys Val Asp
    1115            1120                1125

Pro Ala Ser Gly Glu Glu Leu Arg Pro Gly Ser Ser Ser Ser Ala
    1130            1135                1140

Gln Cys Pro Ser Leu Cys Asn Val Leu Lys Ser Gly Val Leu Ser
    1145            1150                1155

Arg Arg Val Ser Pro Gly Tyr Val Pro Ala Cys Arg Ala Glu Asp
    1160            1165                1170

Gly Gly Phe Ser Pro Val Gln Cys Asp Gln Ala Gln Gly Ser Cys
    1175            1180                1185

Trp Cys Val Met Asp Ser Gly Glu Val Pro Gly Thr Arg Val
    1190            1195                1200

Thr Gly Gly Gln Pro Ala Cys Glu Ser Pro Arg Cys Pro Leu Pro
    1205            1210                1215

Phe Asn Ala Ser Glu Val Val Gly Gly Thr Ile Leu Cys Glu Thr
    1220            1225                1230

Ile Ser Gly Pro Thr Gly Ser Ala Met Gln Gln Cys Gln Leu Leu
    1235            1240                1245

Cys Arg Gln Gly Ser Trp Ser Val Phe Pro Pro Gly Pro Leu Ile
    1250            1255                1260

Cys Ser Leu Glu Ser Gly Arg Trp Glu Ser Gln Leu Pro Gln Pro
    1265            1270                1275

Arg Ala Cys Gln Arg Pro Gln Leu Trp Gln Thr Ile Gln Thr Gln
    1280            1285                1290

Gly His Phe Gln Leu Gln Leu Pro Pro Gly Lys Met Cys Ser Ala
    1295            1300                1305

Asp Tyr Ala Asp Leu Leu Gln Thr Phe Gln Val Phe Ile Leu Asp
    1310            1315                1320

Glu Leu Thr Ala Arg Gly Phe Cys Gln Ile Gln Val Lys Thr Phe
    1325            1330                1335

Gly Thr Leu Val Ser Ile Pro Val Cys Asn Asn Ser Ser Val Gln
    1340            1345                1350

Val Gly Cys Leu Thr Arg Glu Arg Leu Gly Val Asn Val Thr Trp
    1355            1360                1365

Lys Ser Arg Leu Glu Asp Ile Pro Val Ala Ser Leu Pro Asp Leu
    1370            1375                1380

His Asp Ile Glu Arg Ala Leu Val Gly Lys Asp Leu Leu Gly Arg
    1385            1390                1395

Phe Thr Asp Leu Ile Gln Ser Gly Ser Phe Gln Leu His Leu Asp
    1400            1405                1410

Ser Lys Thr Phe Pro Ala Glu Thr Ile Arg Phe Leu Gln Gly Asp
    1415            1420                1425

His Phe Gly Thr Ser Pro Arg Thr Trp Phe Gly Cys Ser Glu Gly
    1430            1435                1440

Phe Tyr Gln Val Leu Thr Ser Glu Ala Ser Gln Asp Gly Leu Gly
    1445            1450                1455
```

```
Cys Val Lys Cys Pro Glu Gly Ser Tyr Ser Gln Asp Glu Glu Cys
1460                1465                1470

Ile Pro Cys Pro Val Gly Phe Tyr Gln Glu Gln Ala Gly Ser Leu
1475                1480                1485

Ala Cys Val Pro Cys Pro Val Gly Arg Thr Thr Ile Ser Ala Gly
1490                1495                1500

Ala Phe Ser Gln Thr His Cys Val Thr Asp Cys Gln Arg Asn Glu
1505                1510                1515

Ala Gly Leu Gln Cys Asp Gln Asn Gly Gln Tyr Arg Ala Ser Gln
1520                1525                1530

Lys Asp Arg Gly Ser Gly Lys Ala Phe Cys Val Asp Gly Glu Gly
1535                1540                1545

Arg Arg Leu Pro Trp Trp Glu Thr Glu Ala Pro Leu Glu Asp Ser
1550                1555                1560

Gln Cys Leu Met Met Gln Lys Phe Glu Lys Val Pro Glu Ser Lys
1565                1570                1575

Val Ile Phe Asp Ala Asn Ala Pro Val Ala Val Arg Ser Lys Val
1580                1585                1590

Pro Asp Ser Glu Phe Pro Val Met Gln Cys Leu Thr Asp Cys Thr
1595                1600                1605

Glu Asp Glu Ala Cys Ser Phe Phe Thr Val Ser Thr Thr Glu Pro
1610                1615                1620

Glu Ile Ser Cys Asp Phe Tyr Ala Trp Thr Ser Asp Asn Val Ala
1625                1630                1635

Cys Met Thr Ser Asp Gln Lys Arg Asp Ala Leu Gly Asn Ser Lys
1640                1645                1650

Ala Thr Ser Phe Gly Ser Leu Arg Cys Gln Val Lys Val Arg Ser
1655                1660                1665

His Gly Gln Asp Ser Pro Ala Val Tyr Leu Lys Lys Gly Gln Gly
1670                1675                1680

Ser Thr Thr Thr Leu Gln Lys Arg Phe Glu Pro Thr Gly Phe Gln
1685                1690                1695

Asn Met Leu Ser Gly Leu Tyr Asn Pro Ile Val Phe Ser Ala Ser
1700                1705                1710

Gly Ala Asn Leu Thr Asp Ala His Leu Phe Cys Leu Leu Ala Cys
1715                1720                1725

Asp Arg Asp Leu Cys Cys Asp Gly Phe Val Leu Thr Gln Val Gln
1730                1735                1740

Gly Gly Ala Ile Ile Cys Gly Leu Leu Ser Ser Pro Ser Val Leu
1745                1750                1755

Leu Cys Asn Val Lys Asp Trp Met Asp Pro Ser Glu Ala Trp Ala
1760                1765                1770

Asn Ala Thr Cys Pro Gly Val Thr Tyr Asp Gln Glu Ser His Gln
1775                1780                1785

Val Ile Leu Arg Leu Gly Asp Gln Glu Phe Ile Lys Ser Leu Thr
1790                1795                1800

Pro Leu Glu Gly Thr Gln Asp Thr Phe Thr Asn Phe Gln Gln Val
1805                1810                1815

Tyr Leu Trp Lys Asp Ser Asp Met Gly Ser Arg Pro Glu Ser Met
1820                1825                1830

Gly Cys Arg Lys Asp Thr Val Pro Arg Pro Ala Ser Pro Thr Glu
1835                1840                1845
```

-continued

```
Ala Gly Leu Thr Thr Glu Leu Phe Ser Pro Val Asp Leu Asn Gln
    1850                1855                1860

Val Ile Val Asn Gly Asn Gln Ser Leu Ser Ser Gln Lys His Trp
    1865                1870                1875

Leu Phe Lys His Leu Phe Ser Ala Gln Gln Ala Asn Leu Trp Cys
    1880                1885                1890

Leu Ser Arg Cys Val Gln Glu His Ser Phe Cys Gln Leu Ala Glu
    1895                1900                1905

Ile Thr Glu Ser Ala Ser Leu Tyr Phe Thr Cys Thr Leu Tyr Pro
    1910                1915                1920

Glu Ala Gln Val Cys Asp Asp Ile Met Glu Ser Asn Ala Gln Gly
    1925                1930                1935

Cys Arg Leu Ile Leu Pro Gln Met Pro Lys Ala Leu Phe Arg Lys
    1940                1945                1950

Lys Val Ile Leu Glu Asp Lys Val Lys Asn Phe Tyr Thr Arg Leu
    1955                1960                1965

Pro Phe Gln Lys Leu Met Gly Ile Ser Ile Arg Asn Lys Val Pro
    1970                1975                1980

Met Ser Glu Lys Ser Ile Ser Asn Gly Phe Phe Glu Cys Glu Arg
    1985                1990                1995

Arg Cys Asp Ala Asp Pro Cys Cys Thr Gly Phe Gly Phe Leu Asn
    2000                2005                2010

Val Ser Gln Leu Lys Gly Gly Glu Val Thr Cys Leu Thr Leu Asn
    2015                2020                2025

Ser Leu Gly Ile Gln Met Cys Ser Glu Glu Asn Gly Gly Ala Trp
    2030                2035                2040

Arg Ile Leu Asp Cys Gly Ser Pro Asp Ile Glu Val His Thr Tyr
    2045                2050                2055

Pro Phe Gly Trp Tyr Gln Lys Pro Ile Ala Gln Asn Asn Ala Pro
    2060                2065                2070

Ser Phe Cys Pro Leu Val Val Leu Pro Ser Leu Thr Glu Lys Val
    2075                2080                2085

Ser Leu Asp Ser Trp Gln Ser Leu Ala Leu Ser Ser Val Val Val
    2090                2095                2100

Asp Pro Ser Ile Arg His Phe Asp Val Ala His Val Ser Thr Ala
    2105                2110                2115

Ala Thr Ser Asn Phe Ser Ala Val Arg Asp Leu Cys Leu Ser Glu
    2120                2125                2130

Cys Ser Gln His Glu Ala Cys Leu Ile Thr Thr Leu Gln Thr Gln
    2135                2140                2145

Pro Gly Ala Val Arg Cys Met Phe Tyr Ala Asp Thr Gln Ser Cys
    2150                2155                2160

Thr His Ser Leu Gln Gly Gln Asn Cys Arg Leu Leu Leu Arg Glu
    2165                2170                2175

Glu Ala Thr His Ile Tyr Arg Lys Pro Gly Ile Ser Leu Leu Ser
    2180                2185                2190

Tyr Glu Ala Ser Val Pro Ser Val Pro Ile Ser Thr His Gly Arg
    2195                2200                2205

Leu Leu Gly Arg Ser Gln Ala Ile Gln Val Gly Thr Ser Trp Lys
    2210                2215                2220

Gln Val Asp Gln Phe Leu Gly Val Pro Tyr Ala Ala Pro Pro Leu
    2225                2230                2235
```

-continued

```
Ala Glu Arg Arg Phe Gln Ala Pro Glu Pro Leu Asn Trp Thr Gly
2240                2245                2250

Ser Trp Asp Ala Ser Lys Pro Arg Ala Ser Cys Trp Gln Pro Gly
2255                2260                2265

Thr Arg Thr Ser Thr Ser Pro Gly Val Ser Glu Asp Cys Leu Tyr
2270                2275                2280

Leu Asn Val Phe Ile Pro Gln Asn Val Ala Pro Asn Ala Ser Val
2285                2290                2295

Leu Val Phe Phe His Asn Thr Met Asp Arg Glu Glu Ser Glu Gly
2300                2305                2310

Trp Pro Ala Ile Asp Gly Ser Phe Leu Ala Ala Val Gly Asn Leu
2315                2320                2325

Ile Val Val Thr Ala Ser Tyr Arg Val Gly Val Phe Gly Phe Leu
2330                2335                2340

Ser Ser Gly Ser Gly Glu Val Ser Gly Asn Trp Gly Leu Leu Asp
2345                2350                2355

Gln Val Ala Ala Leu Thr Trp Val Gln Thr His Ile Arg Gly Phe
2360                2365                2370

Gly Gly Asp Pro Arg Arg Val Ser Leu Ala Ala Asp Arg Gly Gly
2375                2380                2385

Ala Asp Val Ala Ser Ile His Leu Leu Thr Ala Arg Ala Thr Asn
2390                2395                2400

Ser Gln Leu Phe Arg Arg Ala Val Leu Met Gly Gly Ser Ala Leu
2405                2410                2415

Ser Pro Ala Ala Val Ile Ser His Glu Arg Ala Gln Gln Gln Ala
2420                2425                2430

Ile Ala Leu Ala Lys Glu Val Ser Cys Pro Met Ser Ser Ser Gln
2435                2440                2445

Glu Val Val Ser Cys Leu Arg Gln Lys Pro Ala Asn Val Leu Asn
2450                2455                2460

Asp Ala Gln Thr Lys Leu Leu Ala Val Ser Gly Pro Phe His Tyr
2465                2470                2475

Trp Gly Pro Val Ile Asp Gly His Phe Leu Arg Glu Pro Pro Ala
2480                2485                2490

Arg Ala Leu Lys Arg Ser Leu Trp Val Glu Val Asp Leu Leu Ile
2495                2500                2505

Gly Ser Ser Gln Asp Asp Gly Leu Ile Asn Arg Ala Lys Ala Val
2510                2515                2520

Lys Gln Phe Glu Glu Ser Arg Gly Arg Thr Ser Ser Lys Thr Ala
2525                2530                2535

Phe Tyr Gln Ala Leu Gln Asn Ser Leu Gly Gly Glu Asp Ser Asp
2540                2545                2550

Ala Arg Val Glu Ala Ala Ala Thr Trp Tyr Tyr Ser Leu Glu His
2555                2560                2565

Ser Thr Asp Asp Tyr Ala Ser Phe Ser Arg Ala Leu Glu Asn Ala
2570                2575                2580

Thr Arg Asp Tyr Phe Ile Ile Cys Pro Ile Ile Asp Met Ala Ser
2585                2590                2595

Ala Trp Ala Lys Arg Ala Arg Gly Asn Val Phe Met Tyr His Ala
2600                2605                2610

Pro Glu Asn Tyr Gly His Gly Ser Leu Glu Leu Leu Ala Asp Val
2615                2620                2625
```

```
Gln Phe Ala Leu Gly Leu Pro Phe Tyr Pro Ala Tyr Glu Gly Gln
    2630                2635                2640

Phe Ser Leu Glu Glu Lys Ser Leu Ser Leu Lys Ile Met Gln Tyr
    2645                2650                2655

Phe Ser His Phe Ile Arg Ser Gly Asn Pro Asn Tyr Pro Tyr Glu
    2660                2665                2670

Phe Ser Arg Lys Val Pro Thr Phe Ala Thr Pro Trp Pro Asp Phe
    2675                2680                2685

Val Pro Arg Ala Gly Gly Glu Asn Tyr Lys Glu Phe Ser Glu Leu
    2690                2695                2700

Leu Pro Asn Arg Gln Gly Leu Lys Lys Ala Asp Cys Ser Phe Trp
    2705                2710                2715

Ser Lys Tyr Ile Ser Ser Leu Lys Thr Ser Ala Asp Gly Ala Lys
    2720                2725                2730

Gly Gly Gln Ser Ala Glu Ser Glu Glu Glu Glu Leu Thr Ala Gly
    2735                2740                2745

Ser Gly Leu Arg Glu Asp Leu Leu Ser Leu Gln Glu Pro Gly Ser
    2750                2755                2760

Lys Thr Tyr Ser Lys
    2765

<210> SEQ ID NO 2
<211> LENGTH: 12
<212> TYPE: PRT
<213> ORGANISM: Homo sapiens

<400> SEQUENCE: 2

Val Ile Phe Asp Ala Asn Ala Pro Val Ala Val Arg
1               5                   10

<210> SEQ ID NO 3
<211> LENGTH: 8
<212> TYPE: PRT
<213> ORGANISM: Homo sapiens

<400> SEQUENCE: 3

Leu Gly Asp Gln Glu Phe Ile Lys
1               5

<210> SEQ ID NO 4
<211> LENGTH: 12
<212> TYPE: PRT
<213> ORGANISM: Homo sapiens

<400> SEQUENCE: 4

Ser His Gly Gln Asp Ser Pro Ala Val Tyr Leu Lys
1               5                   10

<210> SEQ ID NO 5
<211> LENGTH: 11
<212> TYPE: PRT
<213> ORGANISM: Homo sapiens

<400> SEQUENCE: 5

Phe Pro Leu Gly Glu Ser Phe Leu Val Ala Lys
1               5                   10

<210> SEQ ID NO 6
<211> LENGTH: 14
<212> TYPE: PRT
<213> ORGANISM: Homo sapiens
```

```
<400> SEQUENCE: 6

Gly Gly Ala Asp Val Ala Ser Ile His Leu Leu Thr Ala Arg
1               5                   10

<210> SEQ ID NO 7
<211> LENGTH: 12
<212> TYPE: PRT
<213> ORGANISM: Homo sapiens

<400> SEQUENCE: 7

Phe Leu Gln Gly Asp His Phe Gly Thr Ser Pro Arg
1               5                   10

<210> SEQ ID NO 8
<211> LENGTH: 11
<212> TYPE: PRT
<213> ORGANISM: Homo sapiens

<400> SEQUENCE: 8

Phe Leu Ala Val Gln Ser Val Ile Ser Gly Arg
1               5                   10

<210> SEQ ID NO 9
<211> LENGTH: 13
<212> TYPE: PRT
<213> ORGANISM: Homo sapiens

<400> SEQUENCE: 9

Phe Pro Asp Ala Phe Val Thr Phe Ser Ser Phe Gln Arg
1               5                   10

<210> SEQ ID NO 10
<211> LENGTH: 9
<212> TYPE: PRT
<213> ORGANISM: Homo sapiens

<400> SEQUENCE: 10

Trp Glu Ser Gln Leu Pro Gln Pro Arg
1               5

<210> SEQ ID NO 11
<211> LENGTH: 11
<212> TYPE: PRT
<213> ORGANISM: Homo sapiens

<400> SEQUENCE: 11

Ser Gln Ala Ile Gln Val Gly Thr Ser Trp Lys
1               5                   10

<210> SEQ ID NO 12
<211> LENGTH: 15
<212> TYPE: PRT
<213> ORGANISM: Homo sapiens

<400> SEQUENCE: 12

Lys Val Pro Thr Phe Ala Thr Pro Trp Pro Asp Phe Val Pro Arg
1               5                   10                  15

<210> SEQ ID NO 13
<211> LENGTH: 9
<212> TYPE: PRT
<213> ORGANISM: Homo sapiens

<400> SEQUENCE: 13
```

Thr Ser Gly Leu Leu Ser Ser Trp Lys
1               5

<210> SEQ ID NO 14
<211> LENGTH: 10
<212> TYPE: PRT
<213> ORGANISM: Homo sapiens

<400> SEQUENCE: 14

Leu Ala Leu Gln Phe Thr Thr Asn Pro Lys
1               5                   10

<210> SEQ ID NO 15
<211> LENGTH: 15
<212> TYPE: PRT
<213> ORGANISM: Homo sapiens

<400> SEQUENCE: 15

Leu Arg Asn Glu Asp Leu Gly Leu Pro Pro Leu Phe Pro Pro Arg
1               5                   10                  15

<210> SEQ ID NO 16
<211> LENGTH: 19
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Wherein the Methionine at position 4 is
      optionally oxidized

<400> SEQUENCE: 16

Ala Val Leu Met Gly Gly Ser Ala Leu Ser Pro Ala Ala Val Ile Ser
1               5                   10                  15

His Glu Arg

<210> SEQ ID NO 17
<211> LENGTH: 16
<212> TYPE: PRT
<213> ORGANISM: Homo sapiens

<400> SEQUENCE: 17

Ala Gly Gly Glu Asn Tyr Lys Glu Phe Ser Glu Leu Leu Pro Asn Arg
1               5                   10                  15

<210> SEQ ID NO 18
<211> LENGTH: 19
<212> TYPE: PRT
<213> ORGANISM: Homo sapiens

<400> SEQUENCE: 18

Ala Val Leu Met Gly Gly Ser Ala Leu Ser Pro Ala Ala Val Ile Ser
1               5                   10                  15

His Glu Arg

<210> SEQ ID NO 19
<211> LENGTH: 19
<212> TYPE: PRT
<213> ORGANISM: Homo sapiens

<400> SEQUENCE: 19

Thr Ala Phe Tyr Gln Ala Leu Gln Asn Ser Leu Gly Gly Glu Asp Ser
1               5                   10                  15

Asp Ala Arg

<210> SEQ ID NO 20
<211> LENGTH: 14
<212> TYPE: PRT
<213> ORGANISM: Homo sapiens
<220> FEATURE:
<221> NAME/KEY: MISC_FEATURE
<222> LOCATION: (7)..(7)
<223> OTHER INFORMATION: Wherein the Cysteine at position 7 is
      optionally carbamidomethylated

<400> SEQUENCE: 20

Asn Glu Ala Gly Leu Gln Cys Asp Gln Asn Gly Gln Tyr Arg
1               5                   10

<210> SEQ ID NO 21
<211> LENGTH: 20
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: Wherein the Methionine at position 5 is
      optionally oxidized

<400> SEQUENCE: 21

Arg Ala Val Leu Met Gly Gly Ser Ala Leu Ser Pro Ala Ala Val Ile
1               5                   10                  15

Ser His Glu Arg
            20

<210> SEQ ID NO 22
<211> LENGTH: 17
<212> TYPE: PRT
<213> ORGANISM: Homo sapiens

<400> SEQUENCE: 22

Leu Glu Asp Ile Pro Val Ala Ser Leu Pro Asp Leu His Asp Ile Glu
1               5                   10                  15

Arg

<210> SEQ ID NO 23
<211> LENGTH: 10
<212> TYPE: PRT
<213> ORGANISM: Homo sapiens

<400> SEQUENCE: 23

Ile Met Gln Tyr Phe Ser His Phe Ile Arg
1               5                   10

<210> SEQ ID NO 24
<211> LENGTH: 28
<212> TYPE: PRT
<213> ORGANISM: Homo sapiens

<400> SEQUENCE: 24

Glu Leu Phe Val Asp Ser Gly Leu Leu Arg Pro Met Val Glu Gly Gln
1               5                   10                  15

Ser Gln Gln Phe Ser Val Ser Glu Asn Leu Leu Lys
            20                  25

<210> SEQ ID NO 25
<211> LENGTH: 23
<212> TYPE: PRT

-continued

```
<213> ORGANISM: Homo sapiens

<400> SEQUENCE: 25

Lys Pro Gly Ile Ser Leu Leu Ser Tyr Glu Ala Ser Val Pro Ser Val
1               5                   10                  15

Pro Ile Ser Thr His Gly Arg
            20

<210> SEQ ID NO 26
<211> LENGTH: 16
<212> TYPE: PRT
<213> ORGANISM: Homo sapiens

<400> SEQUENCE: 26

Arg Phe Ser Pro Asp Asp Ser Ala Gly Ala Ser Ala Leu Leu Arg Ser
1               5                   10                  15

<210> SEQ ID NO 27
<211> LENGTH: 15
<212> TYPE: PRT
<213> ORGANISM: Homo sapiens

<400> SEQUENCE: 27

Arg Ser His Gly Gln Asp Ser Pro Ala Val Tyr Leu Lys Lys Gly
1               5                   10                  15

<210> SEQ ID NO 28
<211> LENGTH: 13
<212> TYPE: PRT
<213> ORGANISM: Homo sapiens

<400> SEQUENCE: 28

Arg Leu Ala Ala Gln Ser Thr Leu Ser Phe Tyr Gln Arg
1               5                   10

<210> SEQ ID NO 29
<211> LENGTH: 13
<212> TYPE: PRT
<213> ORGANISM: Homo sapiens

<400> SEQUENCE: 29

Glu Thr Glu Glu Ile Val Ser Ala Ser Asn Ser Ser Arg
1               5                   10
```